US012588911B2

(12) United States Patent
Biscarrat et al.

(10) Patent No.:  US 12,588,911 B2
(45) Date of Patent:  Mar. 31, 2026

(54) DEFLECTABLE SHEATH FOR LEFT ATRIAL APPENDAGE DEVICE, SYSTEM, AND METHOD THEREOF

(71) Applicant: Coherex Medical, Inc., Salt Lake City, UT (US)

(72) Inventors: Marie A. K. Biscarrat, Salt Lake City, UT (US); Tom Ditter, Mission Viejo, CA (US); Juan M. R. Soto, Laguna Hills, CA (US); Kyle W. Swainston, Draper, UT (US); Matthew F. Sheridan, Syracuse, UT (US)

(73) Assignee: Coherex Medical, Inc., Salt Lake City, UT (US)

( * ) Notice: Subject to any disclaimer, the term of this patent is extended or adjusted under 35 U.S.C. 154(b) by 561 days.

(21) Appl. No.: 17/542,929

(22) Filed: Dec. 6, 2021

(65) Prior Publication Data

US 2023/0172611 A1     Jun. 8, 2023

(51) Int. Cl.
| | |
|---|---|
| *A61B 17/12* | (2006.01) |
| *A61M 25/01* | (2006.01) |
| *A61M 25/06* | (2006.01) |

(52) U.S. Cl.
CPC ... *A61B 17/12122* (2013.01); *A61M 25/0147* (2013.01); *A61M 25/0662* (2013.01); *A61B 2017/1205* (2013.01); *A61B 17/12177* (2013.01); *A61M 2025/0681* (2013.01); *A61M 2210/125* (2013.01)

(58) Field of Classification Search
CPC ..... A61B 17/12122; A61B 2017/1205; A61M 25/0147; A61M 25/0662; A61M 2025/0681; A61M 2210/125
See application file for complete search history.

(56) References Cited

U.S. PATENT DOCUMENTS

| | | | | |
|---|---|---|---|---|
| 5,391,147 | A | * | 2/1995 | Imran ................ A61B 18/1492 604/95.04 |
| 5,409,453 | A | * | 4/1995 | Lundquist .............. A61B 10/06 607/99 |
| 8,663,268 | B2 | | 3/2014 | Quinn et al. |
| 9,351,716 | B2 | | 5/2016 | Miles et al. |
| 9,649,115 | B2 | | 5/2017 | Edmiston et al. |
| 9,693,781 | B2 | | 7/2017 | Miles et al. |

(Continued)

FOREIGN PATENT DOCUMENTS

| | | |
|---|---|---|
| WO | WO 2019/019937 | 1/2019 |
| WO | WO 2020/106705 | 5/2020 |

OTHER PUBLICATIONS

English machine translation of the Specification of WO 2019/019937 published Jan. 31, 2019 (22 pages).

*Primary Examiner* — Katherine H Schwiker
*Assistant Examiner* — Zehra Jaffri
(74) *Attorney, Agent, or Firm* — David L. Stott

(57) ABSTRACT

Medical devices, systems and methods for occluding a left atrial appendage of a heart with an implant are provided. In one embodiment, a medical device system includes a sheath for delivering the implant. The sheath includes, at a distal portion of the sheath, first and second deflectable portions that are each independently deflectable relative to first and second pivot locations, respectively. With this arrangement, at least one of the first and second pivot locations are adjustable along a longitudinal length of the distal portion of the sheath.

20 Claims, 13 Drawing Sheets

(56)  References Cited

U.S. PATENT DOCUMENTS

| | | | |
|---|---|---|---|
| 9,883,864 | B2 | 2/2018 | Miles et al. |
| 9,883,936 | B2 | 2/2018 | Sutton et al. |
| 10,064,628 | B2 | 9/2018 | Edmiston et al. |
| 10,631,969 | B2 | 4/2020 | Edmiston et al. |
| 2018/0207404 | A1 | 7/2018 | Worley et al. |
| 2019/0192820 | A1 | 6/2019 | Olson et al. |

* cited by examiner

DEFLECTABLE SHEATH FOR LEFT ATRIAL APPENDAGE DEVICE, SYSTEM, AND METHOD THEREOF

TECHNICAL FIELD

The present invention relates generally to the occlusion of tissue openings or appendages and, more specifically, to devices, systems and methods for occluding or otherwise structurally altering such openings and appendages including, for example, left atrial appendages.

BACKGROUND

The upper chambers of the heart, the atria, have appendages attached to each of them. For example, the left atrial appendage is a feature of all human hearts. The physiologic function of such appendages is not completely understood, but they do act as a filling reservoir during the normal pumping of the heart. The appendages typically protrude from the atria and cover an external portion of the atria. Atrial appendages differ substantially from one to another. For example, one atrial appendage may be configured as a tapered protrusion while another atrial appendage may be configured as a re-entrant, sock-like hole. The inner surface of an appendage is conventionally trabeculated with cords of muscular cardiac tissue traversing its surface with one or multiple lobes.

The atrial appendages appear to be inert while blood is being pumped through them during normal heart function. In other words, the appendages do not appear to have a noticeable effect on blood pumped through them during normal heart function. However, in cases of atrial fibrillation, when the atria go into arrhythmia, blood may pool and thrombose inside of the appendages. Among other things, this can pose a stroke risk when it occurs in the left appendage since the thrombus may be pumped out of the heart and into the cranial circulation once normal sinus rhythm is restored following arrhythmia events.

Historically, appendages have sometimes been modified surgically to reduce the risk imposed by atrial fibrillation. In recent years devices which may be delivered percutaneously into the left atrial appendage have been introduced. The basic function of these devices is to exclude the volume within the appendage with an implant which then allows blood within the appendage to safely thrombose and then to be gradually incorporated into cardiac tissue. This process, coupled with the growth of endothelium over the face of the device, can leave a smooth, endothelialized surface where the appendage is located. In comparison to surgical procedures, devices implanted percutaneously are a less invasive means for addressing the problems associated with the left atrial appendage.

However, due to the wide variability of the ostium size and volume of the left atrial appendage, most current implantable devices include structure that cannot meet such variability, resulting in inadequate devices for many left atrial appendage anatomies. One important aspect to minimize the effects in the variability of ostium size is to ensure the medical device is appropriately oriented relative to the ostium. As such, it would be advantageous to provide a percutaneous system, method and/or device that addresses, for example, the issues relating to the adjustability and orientation of implantable devices within the left atrial appendage in order to provide high success in left atrial appendage modification.

A variety of features and advantages will be apparent to those of ordinary skill in the art upon reading the description of various embodiments set forth below.

BRIEF SUMMARY OF THE INVENTION

Embodiments of the present invention are directed to various devices, systems and methods for delivering a medical device. In one embodiment, a medical device system for occluding a left atrial appendage of a heart is provided. The medical device includes a delivery catheter and a sheath, the delivery catheter includes a medical device coupled adjacent a delivery catheter distal end of the delivery catheter. The sheath extends with a wall between a distal end and a proximal end with a central lumen and central axis defined in the sheath along a longitudinal length of the sheath such that the medical device and delivery catheter are advanceable through the central lumen of the sheath. Further, the sheath defines a concentric lumen therein so as to extend along the wall, the sheath being deflectable with a first deflectable portion relative to a first pivot location along a distal portion of the sheath and the sheath being deflectable with a second deflectable portion relative to a second pivot location along the distal portion of the sheath. With this arrangement, at least one of the first pivot location and the second pivot location of the first and second deflectable portions, respectively, is adjustable along the longitudinal length of the distal portion of the sheath.

In another embodiment, upon the at least one of the first and second pivot locations being adjusted, a radius of at least one of the first and second deflectable portions is adjusted. In a further embodiment, the radius increases upon the at least one of the first and second pivot locations being moved proximally along the length of the sheath and, the radius decreases upon the at least one of the first and second pivot locations being moved distally along the length of the sheath.

In another embodiment, the sheath includes a slidable tubular member with a distal end, the slidable tubular member positioned within the concentric lumen defined in the sheath, the distal end of the slidable tubular member defining at least one of the first and second pivot locations of the sheath. In a further embodiment, the slidable tubular member is linearly slidable within the concentric lumen to change the at least one of the first and second pivot locations of the sheath.

In another embodiment, the slidable tubular member includes openings defined therein, the openings sized and configured to hold control wires therein so that the control wires extend distal of at least one of the first and second pivot locations for controlling deflection of at least one of the first and second deflectable portions, respectively. In another embodiment, the first and second deflectable portions are deflectable in multiple directions. In still another embodiment, the sheath is separately and independently deflectable relative to the first pivot location and the second pivot location along the sheath.

In another embodiment, the first and second deflectable portions are deflectable with a control actuator integrated in a sheath handle of the sheath, the control actuator including at least one of a rack and pinion system, a pneumatic system, and a hydraulic system. In another embodiment, the at least one of the first and second deflectable portions are deflectable with multiple wires extending through the concentric lumen along the longitudinal length of the sheath, the multiple wires having a first portion and a second portion with a transition point between the first and second portions, the first portion being distal of and more flexible than the second portion, the transition point of the multiple wires being moveable along the longitudinal length to change a radius of the at least one of the first and second deflectable portions.

In accordance with another embodiment of the present invention, a medical device system for occluding a left atrial appendage of a heart with an implant, the implant positioned adjacent a delivery catheter, is provided. The medical device includes a sheath such that the sheath extends with a wall between a distal end and a proximal end with a central lumen and central axis defined in the sheath along a longitudinal length of the sheath such that the implant and delivery catheter are advanceable through the central lumen of the sheath. The sheath defines a concentric lumen therein so as to extend along the wall, the sheath being deflectable with a first deflectable portion relative to a first pivot location along a distal portion of the sheath and the sheath being deflectable with a second deflectable portion relative to a second pivot location along the distal portion of the sheath. With this arrangement, at least one of the first pivot location and the second pivot location of the first and second deflectable portions, respectively, is adjustable along the longitudinal length of the distal portion of the sheath.

In another embodiment, upon the at least one of the first and second pivot locations being adjusted, a radius of at least one of the first and second deflectable portions is adjusted. In a further embodiment, the radius increases upon the at least one of the first and second pivot location being moved proximally along the length of the sheath and, wherein the radius decreases upon the at least one of the first and second pivot location being moved distally along the length of the sheath.

In another embodiment, the sheath includes a slidable tubular member with a distal end, the slidable tubular member positioned within the concentric lumen defined in the sheath, the distal end of the slidable tubular member defining at least one of the first and second pivot locations of the sheath. In still another embodiment, the slidable tubular member is linearly slideable within the concentric lumen to change the at least one of the first and second pivot locations of the sheath. In another embodiment, the slidable tubular member includes openings defined therein, the openings sized and configured to hold control wires therein so that the control wires extend distal of at least one of the first and second pivot locations for controlling deflection of at least one of the first and second deflectable portions, respectively.

In another embodiment, the first and second deflectable portions are deflectable in multiple directions. In still another embodiment, the sheath is separately and independently deflectable relative to the first pivot location and the second pivot location along the sheath. In another embodiment, the first and second deflectable portions are deflectable with a control actuator integrated in a sheath handle of the sheath, the control actuator including at least one of a rack and pinion system, a pneumatic system, an a hydraulic system. In another embodiment, at least one of the first and second deflectable portions are deflectable with multiple wires extending through the concentric lumen along the longitudinal length of the sheath, the multiple wires having a first portion and a second portion with a transition point between the first and second portions, the first portion being distal of and more flexible than the second portion, transition point of the multiple wires being moveable along the longitudinal length to change a radius of the at least one of the first and second deflectable portions.

In accordance with another embodiment of the present invention, a method for axially aligning a distal end of medical device delivery system with an ostium of a left atrial appendage of a heart is provided. The method steps include positioning a distal end of a sheath adjacent the left atrial appendage of the heart, the sheath extending with a wall between a distal end and a proximal end with a central lumen and central axis defined in the sheath along a longitudinal length of the sheath such that an implant and delivery catheter are advanceable through the central lumen of the sheath, the sheath defining a concentric lumen therein so as to extend along the wall, the sheath being deflectable with a first deflectable portion relative to a first pivot location along a distal portion of the sheath and the sheath being deflectable with a second deflectable portion relative to a second pivot location along the distal portion of the sheath; and adjusting at least one of the first pivot location and the second pivot location of the first and second deflectable portions, respectively, along the longitudinal length of the distal portion of the sheath.

In another embodiment, the adjusting step includes adjusting a radius of at least one of the first and second deflectable portions. In still another embodiment, the adjusting the radius step includes increasing the radius of the at least one of the first and second deflectable portions by moving the at least one of the first and second pivot locations proximally along the length of the sheath. In yet another embodiment, the adjusting step includes sliding a tubular member within the concentric lumen such that a distal end of the tubular member corresponds with at least one of the first and second pivot locations of the first and second deflectable portions, respectively. In another embodiment, the adjusting step includes moving one or more control wires proximally or distally to move the at least one of the first and second pivot locations along the length of the sheath.

BRIEF DESCRIPTION OF THE SEVERAL VIEWS OF THE DRAWINGS

The foregoing and other advantages of the invention will become apparent upon reading the following detailed description and upon reference to the drawings in which.

DETAILED DESCRIPTION OF THE INVENTION

Figure 1:
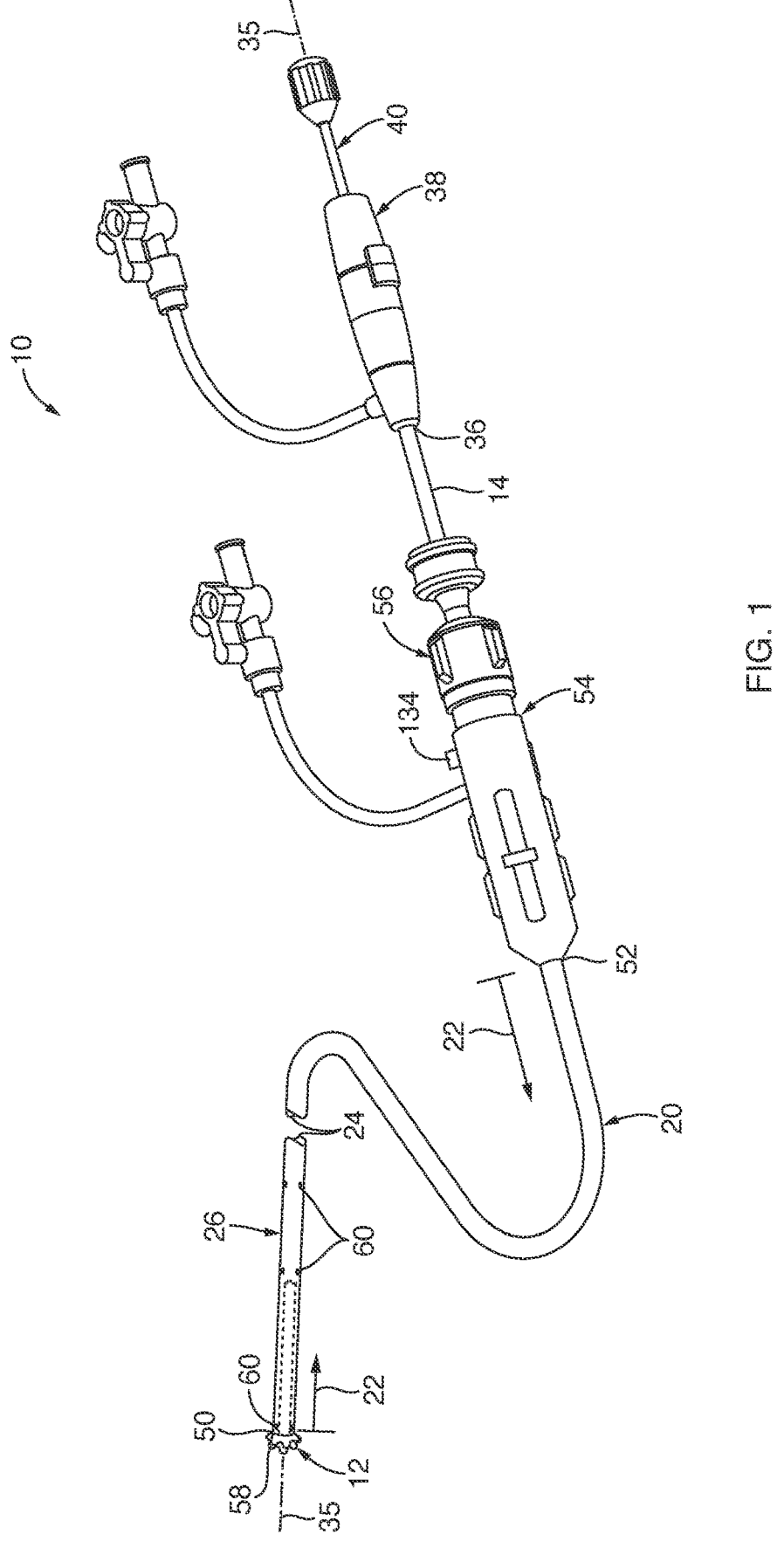
FIG. 1 is a perspective view of a medical device delivery system, depicting a medical device at least partially constricted within a sheath and coupled to a pusher catheter that extends through the sheath, according to one embodiment of the present invention.

Referring to FIGS. 1-3 and 8, a medical device delivery system 10 sized and configured for delivering a medical device 12 is provided. The medical device delivery system 10 may be employed in interventional procedures for percutaneously closing and modifying an opening or cavity such as, for example, a left atrial appendage within a heart (not shown). The medical device delivery system 10 may include a pusher catheter 14 with the medical device 12 removably coupled adjacent to a distal end 16 of the pusher catheter 14. The medical device delivery system 10 may also include a sheath 20 sized and configured to be employed with the pusher catheter 14 and the medical device 12. Further, such sheath 20 may be sized and configured to appropriately orient the medical device 12 prior to being implanted in, for example, an ostium of the left atrial appendage of the heart. The sheath 20 may extend with a longitudinal length 22 such that the medical device 12 and pusher catheter 14 may be advanceable through a central lumen 24 and of the sheath 20. The medical device delivery system 10 may define an axis 35 or central axis extending longitudinally through the pusher catheter 14 and the sheath 20 so as to extend centrally along the central lumen 24 of the sheath 20.

Further, the sheath 20 may be manipulated in a deflectable manner along a distal end portion 26 such that the sheath 20 may extend with a first deflectable portion 28 relative to a first pivot location 32 along the distal end portion 26 of the sheath 20 as well as extend with a second deflectable portion 30 relative to a second pivot location 34 along the distal end portion 26 of the sheath 20. In one embodiment, to further assist the sheath 20 being appropriately oriented for implanting the medical device 12, at least one (or both) of the first pivot location 32 and the second pivot location 34 of the first and second deflectable portions 28, 30, respectively, may be adjustable along the longitudinal length 22 of the distal end portion 26 of the sheath 20.

Figure 2:
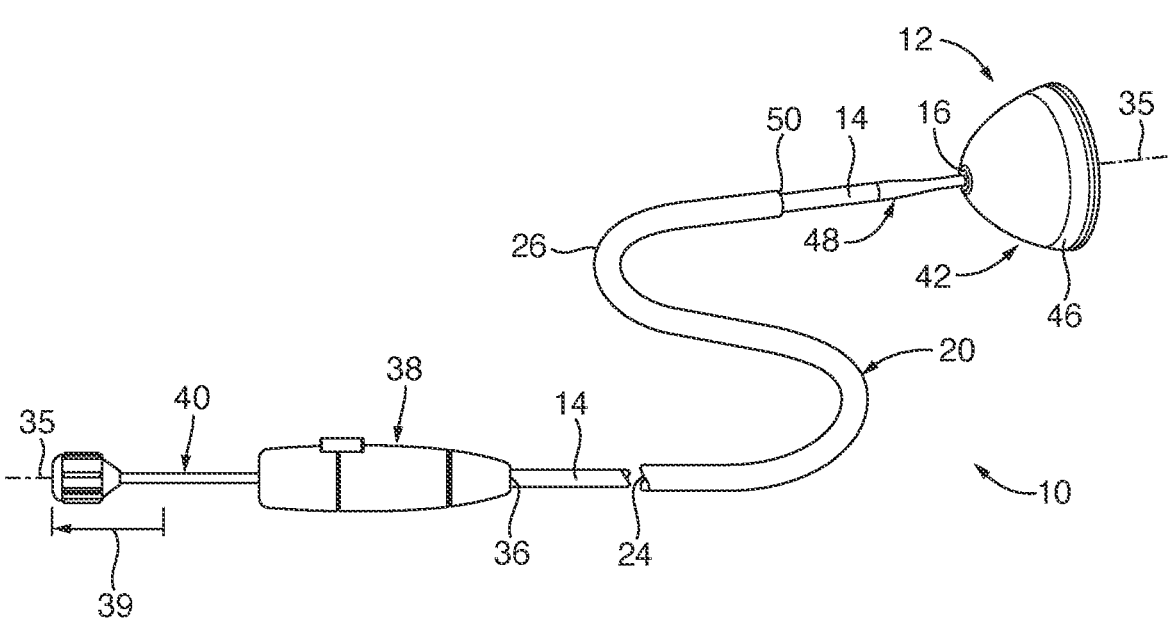
FIG. 2 is a perspective view of the medical device delivery system, depicting the medical device in a partially deployed position with the sheath withdrawn from the medical device, according to another embodiment of the present invention.
Figure 3:
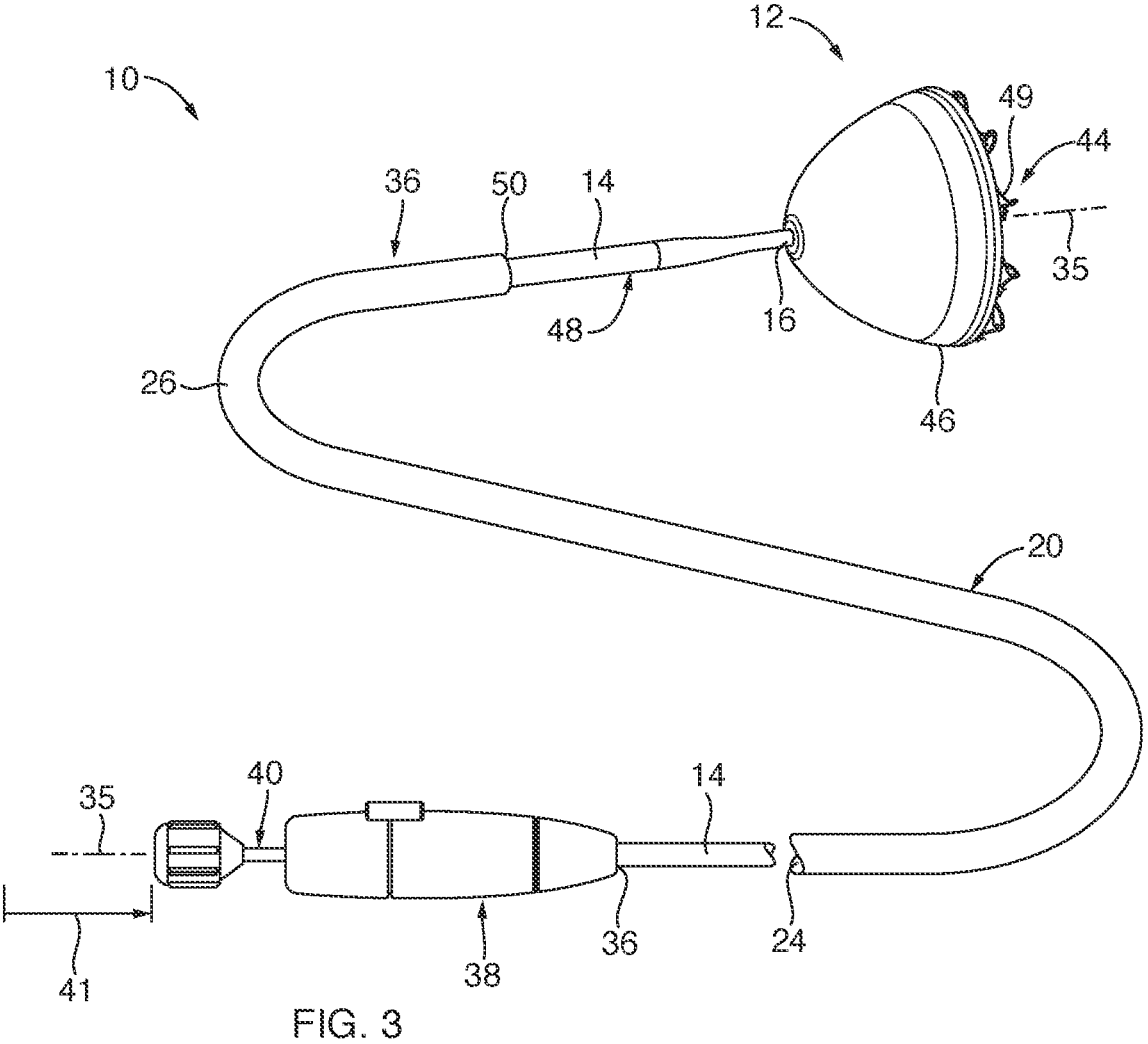
FIG. 3 is a perspective view of the medical device delivery system, depicting the medical device in a deployed position and coupled adjacent a distal end of the pusher catheter, according to another embodiment of the present invention.

Now with reference to FIGS. 1-3, as previously set forth, the medical device delivery system 10 includes the pusher catheter 14. The pusher catheter 14 may extend between the distal end 16 and a proximal end 36, the medical device 12 being removably coupled adjacent the distal end 16 of the pusher catheter 14. The proximal end 36 of the pusher catheter 14 may be coupled to a pusher catheter handle 38. Such pusher catheter handle 38 may be sized and configured to deploy the medical device 12 from a constricted position (FIG. 1) to a deployed position (FIG. 3) such that the medical device 12, at least partially, may self-expand upon being released from the sheath 20 (FIG. 2). Such movement of the medical device 12 between the constricted and deployed positions may be partially employed with an anchor actuator 40 of the pusher catheter handle 38 such that the anchor actuator 40 may be moved between a proximal position (FIG. 2) and a distal position (FIG. 3), as shown with arrows 39 and 41, respectively.

In some embodiments, the medical device 12 employed with the sheath 20 and pusher catheter 14 may include an occluder portion 42 and an anchor portion 44. The occluder portion 42 and the anchor portion 44 may be separately and independently deployed from the sheath 20 and the pusher catheter 14, respectively. The occluder portion 42 may include occluder frame segments (now shown) that support a tissue growth member 46. Such tissue growth member 46 may extend along sides of the occluder frame segments. The tissue growth member 46 may be in the form of an occlusive member, but may also be in the form of a filter member, a mesh member, a membrane or any other structure, or combinations thereof, sized and configured to promote tissue in-growth therein. Further, the tissue growth member 46 may be formed from one or more polymeric materials, such as ePTFE and/or a polyurethane foam, or any other suitable tissue in-growth material.

The anchor portion 44 of the medical device 12 may be actuated between a constricted position (FIGS. 1 and 2) and a deployed position (FIG. 3) via the anchor actuator 40 associated with the pusher catheter handle 38. In the constricted position, the anchor portion 44 is pivoted within an end portion 48 of the pusher catheter 14 with a portion of anchor frame segments extending outside the pusher catheter 14 and pivotably coupled to the occluder frame segments. Further, in the constricted position, the anchor actuator 40 may be in a proximal position, as depicted in FIG. 2. Upon the anchor portion 44 being in the deployed position, the anchor actuator 40 may be in a distal position by manually moving the anchor actuator from the proximal position to the distal position, as shown in FIGS. 2 and 3.

With reference to FIG. 1, as previously set forth, the medical device delivery system 10 may include the sheath 20. Such sheath 20 may extend between a distal end 50 and a proximal end 52. The proximal end 52 of the sheath 20 may be associated with a sheath handle 54 and a valve 56. The sheath 20 may also define the central lumen 24 extending along the length 22 of the sheath 20, the central lumen 24 sized and configured to advance the medical device 12 and pusher catheter 14 therethrough. The medical device 12 may be constricted and advanced through the central lumen 24 to be positioned adjacent the distal end 50 of the sheath 20. In some embodiments, an atraumatic portion 58 or cushion portion of the occluder portion 42 (FIG. 2) of the medical device 12 may extend slightly distal from the distal end 50 of the sheath 20. As such, the atraumatic portion 58 of the medical device delivery system 10 may assist in minimizing the puncture of tissue in the heart or other anatomy prior to and during deployment of the medical device 12. The distal end 50 of the sheath 20 (or portions adjacent thereto) may include one or more markers 60 to assist physicians to understand the orientation of the distal end portion 26 of the sheath 20. As such, upon the distal end portion 26 of the sheath 20 as well as the medical device 12 being advanced through the vasculature and into the left atrium of the heart, the physician can determine if the orientation is appropriate for deploying the medical device 12. If the physician determines the distal end portion 26 should be oriented differently, the physician may actuate various portions of the sheath handle 54 (discussed in further detail herein) to deflect the first and second deflectable portions 28, 30 (FIG. 8) along the distal end portion 26 of the sheath 20 to a desired position, viewable via the one or more markers 60. Upon the physician being satisfied with the orientation of the distal end portion 26 of the sheath 20, the occluder portion 42 (FIG. 2) may be deployed from the distal end 50 of the sheath 20 by moving the sheath 20 proximally relative to the pusher catheter 14. As the sheath 20 is moved proximally over the pusher catheter 14, the occluder portion 42 immediately self-expands to an occluder deployed position, as shown in FIG. 2. The physician may then position the occluder portion 42 within the ostium of the left atrial appendage. The anchor portion 44 may then be moved to the deployed position by moving the anchor actuator distally, which in turn, may move and pivot the anchor portion 44 to the deployed position, as depicted in FIG. 3. Further, one version of the medical device delivery system 10 that may include many of the components set forth herein, such as the medical device 12, the pusher catheter 14, and portions of the sheath 20 is disclosed in commonly assigned U.S. patent application Ser. No. 15/438, 650, filed on Feb. 21, 2017, now issued as U.S. Pat. No. 10,631,969, entitled MEDICAL DEVICE FOR MODIFI-CATION OF LEFT ATRIAL APPENDAGE AND RELATED SYSTEMS AND METHODS, the disclosure of which is incorporated by reference herein in its entirety.

Figure 4:
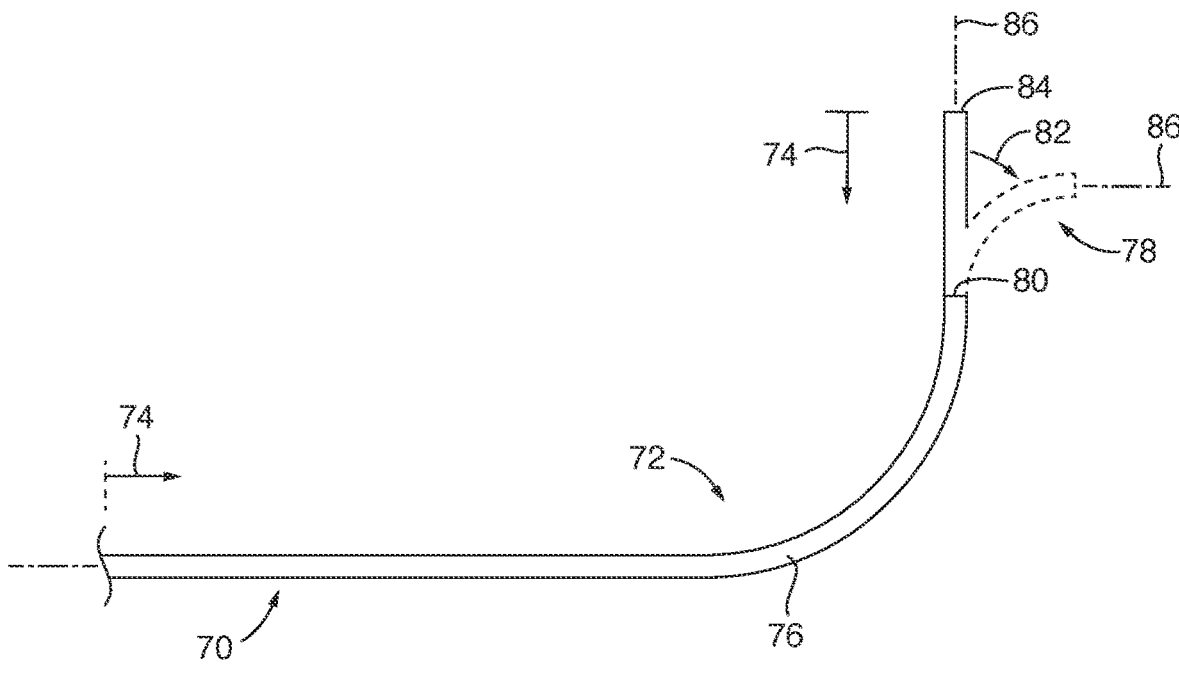
FIG. 4 is a side view of a distal portion of the sheath, depicting the sheath having a pre-defined curve and a deflectable portion, according to another embodiment of the present invention.
Figure 5:
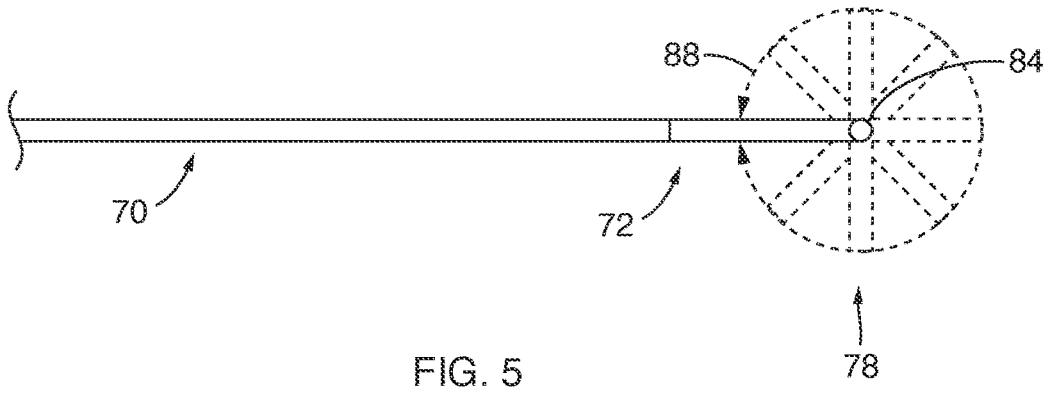
FIG. 5 is a top view of the distal portion of the sheath of FIG. 4, depicting a deflection range of the deflectable portion of the sheath, according to another embodiment of the present invention.

With reference to FIGS. 4 and 5, in one embodiment, a distal end portion 72 of a sheath 70 may extend with at least one deflectable portion along a longitudinal length 74 of the sheath 70. For example, the distal end portion 72 of the sheath 70 may include a predefined curve 76 and a deflectable portion 78. In a relaxed condition of the sheath 70, the predefined curve 76 may be bent or curved relative to other portions of the sheath 70 that may be proximal or distal of the predefined curve 76 of the sheath 70. Such other portions may extend substantially straight in the relaxed condition. Further, the sheath 70 may be flexible so as to be moveable along its length 74 (including along the predefined curve 76) to facilitate the sheath 70 to move in a curved or flexible manner as needed as the sheath 70 is being advanced through the vasculature, for example.

As previously set forth, the distal end portion 72 of the sheath 70 may include the deflectable portion 78. Such deflectable portion 78 may pivot at a pivot location 80 or pivot point along the distal end portion 72 of the sheath 70. In one embodiment, the deflectable portion 78 may be controlled by a physician at the sheath handle 54 (FIG. 1) and may deflect via wires extending through one or more lumens defined in the wall of the sheath 70, discussed further herein. The deflectable portion 78 may be deflectable relative to an adjacent portion immediately proximal of the pivot location 80 such that the deflectable portion 78 may pivot or deflect from the pivot location 80 up to about 90 degrees, as depicted by arrow 82 in FIG. 4. Such adjacent portion of the sheath 70 may be more rigid than the deflectable portion 78 of the sheath 70 along the distal end portion 72. Further, the deflectable portion 78 may deflect in multiple directions and orientations at the pivot location 80 so that a distal end 84 of the sheath 70 can be oriented to extend in any direction within a span 88 of 360 degrees looking downward upon the distal end 84 of the sheath 70, as depicted in FIG. 5. In this manner, as shown with the deflectable portion 78 in dashed lines, such deflectable portion may move from the pivot location 80 up to about 90 degrees, similar to that shown in FIG. 4, at the multiple directions and orientations, as depicted in FIG. 5. With this arrangement, the predefined curve 76 of the sheath 80 may be configured to position the distal end 84 of the sheath 70 adjacent the left atrial appendage and the deflectable portion 78 may be configured to substantially orient the distal end 84 the sheath 70 substantially toward the ostium of the left atrial appendage, as desired by the physician. In other words, the deflectable portion 78 at the distal end portion 72 of the sheath 70 may be manipulated in its orientation so that an axis 86 extending from the distal end 84 of the sheath 70 may be substantially or generally aligned with an axis of the ostium of the left atrial appendage, or, at the least, the axis 86 of the sheath 70 may be moved toward alignment with the axis of the ostium of the left atrial appendage.

Figure 6:
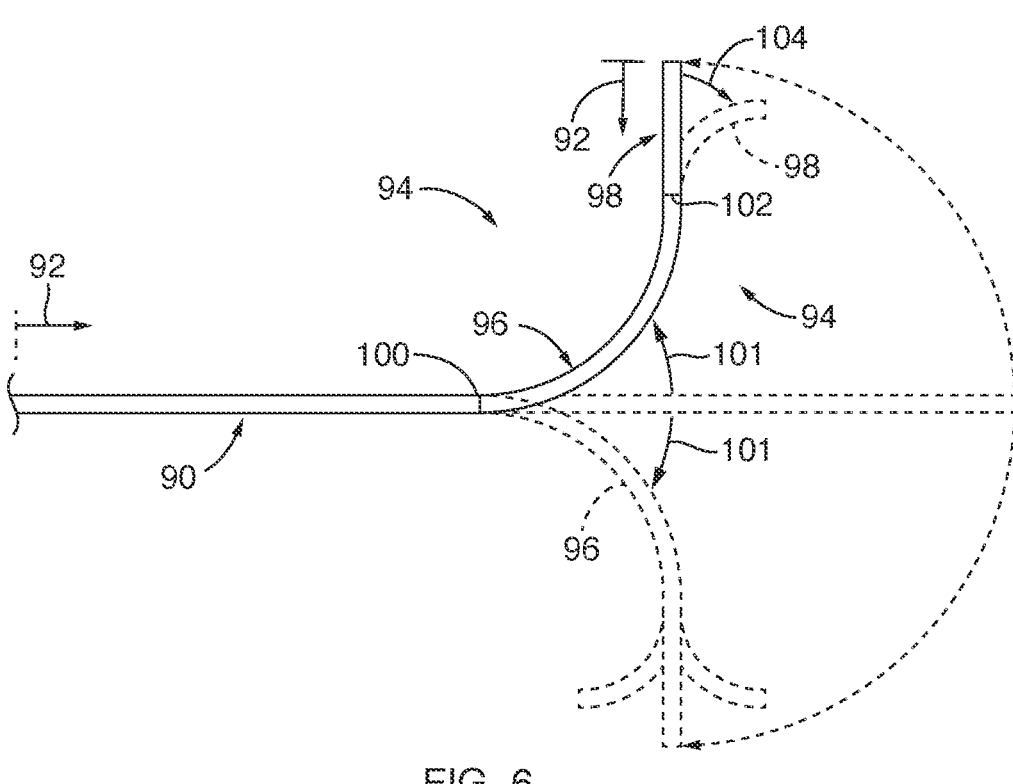
FIG. 6 a side view of another embodiment of a distal portion of the sheath, depicting the sheath having a first deflectable portion and a second deflectable portion, according to the present invention.
Figure 7:
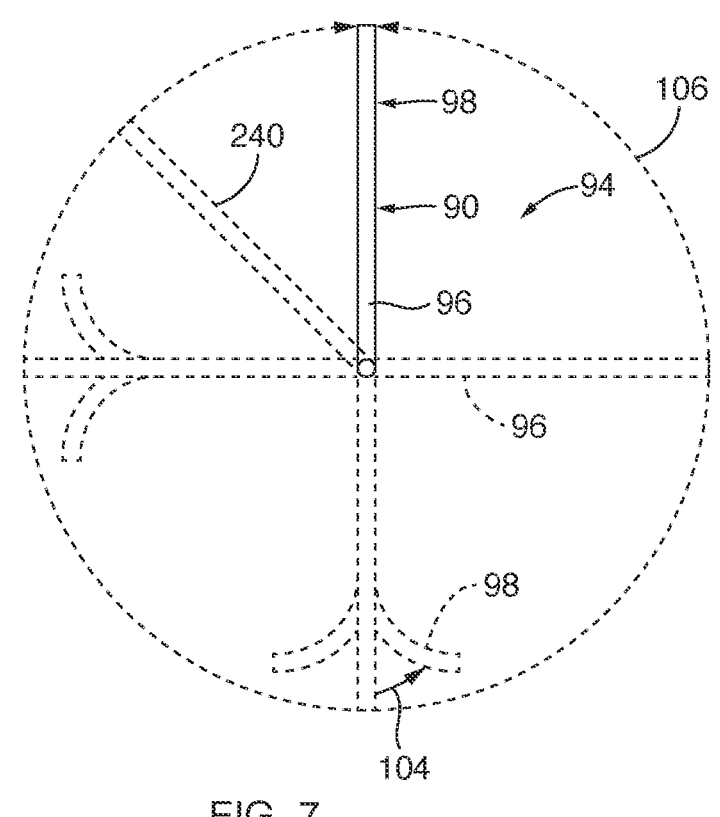
FIG. 7 is an end view of the distal portion of the sheath of FIG. 6, depicting a first deflection range of the first deflectable portion of the sheath and a second deflection range of the second deflectable portion of the sheath, according to another embodiment of the present invention.

Now with reference to FIGS. 6 and 7, another embodiment of a sheath 90 having multiple deflectable portions is provided. In this embodiment, instead of having a predefined curve in the sheath 90, the sheath 90 may have an additional deflectable portion. For example, along a length 92 of the sheath 90, such as a distal end portion 94 of the sheath 90, the sheath 90 may include a first deflectable portion 96 and a second deflectable portion 98. The first deflectable portion 96 may be at a more proximal position along the length 92 of the distal end portion 94 of the sheath 90 than the second deflectable portion 98. The first deflectable portion 96 may include a first pivot location 100, from which the first deflectable portion 96 may pivot and deflect to various positions and orientations, as shown by arrow 101. For example, at and from the first pivot location 100, the first deflectable portion 96 of the sheath 90 may deflect up to about 90 degrees, as depicted in FIG. 6, and be moveable in various directions (as shown by the first deflectable portion 96 in dashed lines) so as to be moveable within a span 106 in multiple directions or orientations. Such span 103 may extend up to 360 degrees, as depicted in FIG. 7.

With continued reference to FIGS. 6 and 7, the second deflectable portion 98 may be similarly located as the deflectable portion 78 (FIG. 4) of the previous embodiment. That is, the second deflectable portion 98 may include the second pivot location 102 or pivot point, at which the second deflectable portion 98 may pivot from the second pivot location 102 up to about 90 degrees, as shown by arrow 104. Further, similar to the previous embodiment, the second deflectable portion 98 may pivot at the second pivot location 102 in multiple directions or orientations, as shown in dashed lines in FIGS. 6 and 7, so as to be able to move within a span of 360 degrees (similar to span 88 of FIG. 5). Further, in this embodiment, the first and second deflectable portions 96, 98 may be moved and manipulated into various positions and orientations. As in the previous embodiment, manipulation of the sheath 90 may be controlled from the sheath handle 54 (FIG. 1) and may be implemented with wires extending through annular lumens defined in the side wall of the sheath 90. Further, the first and second deflectable portions 96, 98 of the sheath 90 may be more flexible than other portions of the sheath 90, such as the length 92 of the sheath 90 that may be proximal of the distal end portion 94 of the sheath 90. In this manner, the sheath 90 may be manipulated along the length 92 of the distal end portion 94 of the sheath 90 by manipulating the first and second deflectable portions 96, 98 of the sheath 90 to pivot and deflect at the respective first and second pivot locations 100, 102.

Figures 8, 8A:
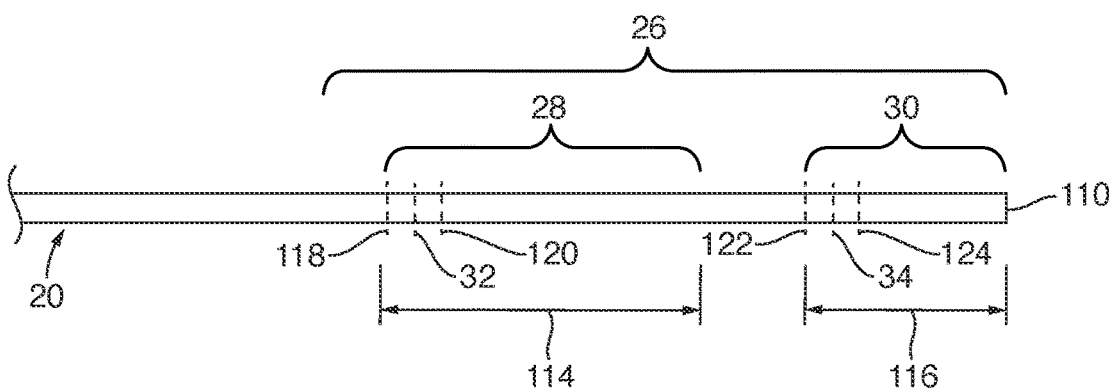
FIG. 8 is a side view of another embodiment of the sheath of the medical device delivery system, depicting the sheath having one or more adjustable pivot locations for the first and/or second deflectable portions of the sheath, according to the present invention.
FIG. 8A is a side view of a distal portion of the sheath, depicting lengths of the first and second deflectable portions along the distal portion of the sheath in non-deflected positions, according to another embodiment of the present invention.

Now with reference to FIGS. 8 and 8A, another embodiment of the sheath 20 with the distal end portion 26 having multiple deflectable portions and deflectable positions along the length 22 of the sheath 20 is provided. The sheath 20 may extend between a distal end 110 and a proximal end 112, the distal end 110 being a terminal end and the proximal end 112 being associated with the sheath handle 54. Similar to previous embodiments, the distal end portion 26 may include a first deflectable portion 28 and a second deflectable portion 30 each of which may be deflectably moveable from respective first and second pivot locations 32, 34. Further, the distal end portion 26 of the sheath 20 may extend to define a first deflectable length 114 and a second deflectable length 116 each of which may correspond with the first and second deflectable portions 28, 30, respectively. In this embodiment, the first and second pivot locations 32, 34 may be moveable proximally or distally along the respective first and second deflectable lengths 114, 116 of the distal end portion 26 of the sheath 20. For example, the first pivot location 32 may be moved proximally to a proximal first pivot location 118, as shown by arrow 119, and may be moved distally to a distal first pivot location 120, as shown by arrow 121. As such, upon changing the first pivot location 32 either proximally or distally, the first deflectable length 114 may effectively change either longer or shorter, respectively. Similarly, the second pivot location 30 may be moved proximally and distally to a respective proximal second pivot location 122 and a distal second pivot location 124, which may change the effective length of the second deflectable length 116 of the second deflectable portion 30. In this manner, the first and second deflectable lengths 114, 116 may be adjustable to either be longer or shorter so that, upon actuating the first and/or second deflectable portions 28, 30, a radius of the first and second deflectable portions 28, 30 may also be adjusted relative to their corresponding effective first and second deflectable lengths 114, 116. In another embodiment, the sheath 20, along the distal end portion 26, or along the first and second deflectable lengths 114, 116 may be more flexible than other portions of the sheath 20 to assist in the actuation of the first and second deflectable portions 28, 30.

In another embodiment, the distal end portion 26 of the sheath 20 may include one or more markers 60. Such markers 60 may be integrated with the distal end portion 26 of the sheath 20 at strategically located positions so that a physician can better understand the location and orientation of the distal end portion 26 of the sheath 20 relative to adjacently positioned anatomy, such as an ostium of a left atrial appendage of the heart. In this manner, as the sheath is advanced through the vasculature toward the heart and into the heart, the markers 60 may assist the physician in viewing the location and orientation of the distal end and the distal end portion of the sheath, by employing imaging techniques, as known to one of ordinary skill in the art. Such markers may be made from radiopaque material, such as platinum, gold, tantalum, or alloys thereof, or any other suitable radiopaque materials that are biocompatible, as known to one of ordinary skill in the art.

Further, the sheath handle 54 may include various actuators and knobs sized and configured to manipulate the distal end portion 26 the sheath 20. For example, the sheath handle 54 may include a first knob 126 and a second knob 128, the first and second knobs 126, 128 sized and configured to be moveable so as to actuate or deflect the first and/or second deflectable portions 28, 30 of the sheath 20. Further, the sheath handle 54 may include a finger 130, the finger 130 moveable proximally, as shown by arrow 131, or distally, as shown by arrow 133, to correspondingly move one of the first and second pivot locations 32, 34 of the first and second deflectable portions 28, 30, respectively. The sheath handle 54 may also include a switch 132. Such switch 132 may be moved between a first position and a second position by being, for example, pushed inward or depressed. In one embodiment, upon the switch 132 being in the first position, movement of the finger 130 may correspond to move the first pivot location 32 along the length 22 of the sheath 20. Similarly, upon the switch 132 being moved to the second position, movement of the finger 130 may correspond to move the second pivot location 34 along the length 22 of the sheath 20. In a similar manner, the sheath handle 54 may include a second switch 134 that may be moved between first and second positions. For example, upon the second switch 134 being moved to the first position, movement of the first and second knobs 126, 128 may correspond to actuate or deflect the first deflectable portion 28 of the sheath. Further, upon the second switch 134 being moved to the second position, movement of the first and second knobs 126, 128 may correspond to actuate or deflect the second deflectable portion 30 of the sheath 20. With this arrangement, the various actuators and knobs and other components of the sheath handle 54 may be moved by a physician so that the physician can manipulate the distal end portion 26 of the sheath handle 54. In this manner, the physician may view the distal end portion 26 of the sheath 20 with imaging techniques via the one or more markers 60 so that the physician may appropriately position and orient the distal end portion 26 and distal end 110 of the sheath 20 so that a medical device 12 (FIG. 3) may be deployed therefrom and be more effectively implanted at a target location, such as within the ostium of the left atrial appendage.

In one embodiment, upon the switch 132 being in the first position, the first pivot location 32 may be moved proximally or distally. Such proximal or distal movement of the first pivot location 32 may effectively change a first deflectable length 114 of the first deflectable portion 28 such that a radius of the first deflectable portion 28 may be adjustable. For example, upon moving the first pivot location 32 in a proximal direction, the first deflectable length 114 may be increased so as to define a proximal first pivot location 118, which may define a proximal first radius 136 of the first deflectable portion 28. On the other hand, upon moving the first pivot location 32 in a distal direction, the first deflectable length 114 may be decreased so as to define a distal first pivot location 120, which may define a distal first radius 138 of the first deflectable portion 28 28. Because the effective length of the first deflectable portion is longer upon the pivot being at the proximal first pivot location compared to the distal first pivot location, the corresponding proximal first radius 136 may be larger than the distal first radius 138. In other words, a physician may manipulate the radius of the first deflectable portion 28 by adjusting the first pivot location 32 either proximally or distally to respectively increase or decrease the radius of the first deflectable portion 28. Similarly, the second pivot location 34 may be moved proximally or distally along the length 22 of the sheath 20 to manipulate the radius length of the second deflectable portion 30. In this manner, the physician may adjust the radius of the first and second deflectable portions 28, 30 in order to best position and orient the distal end portion 26 and the distal end 110 of the sheath 20 relative to the ostium of the left atrial appendage for implanting a medical device therein.

Figures 9, 9A:
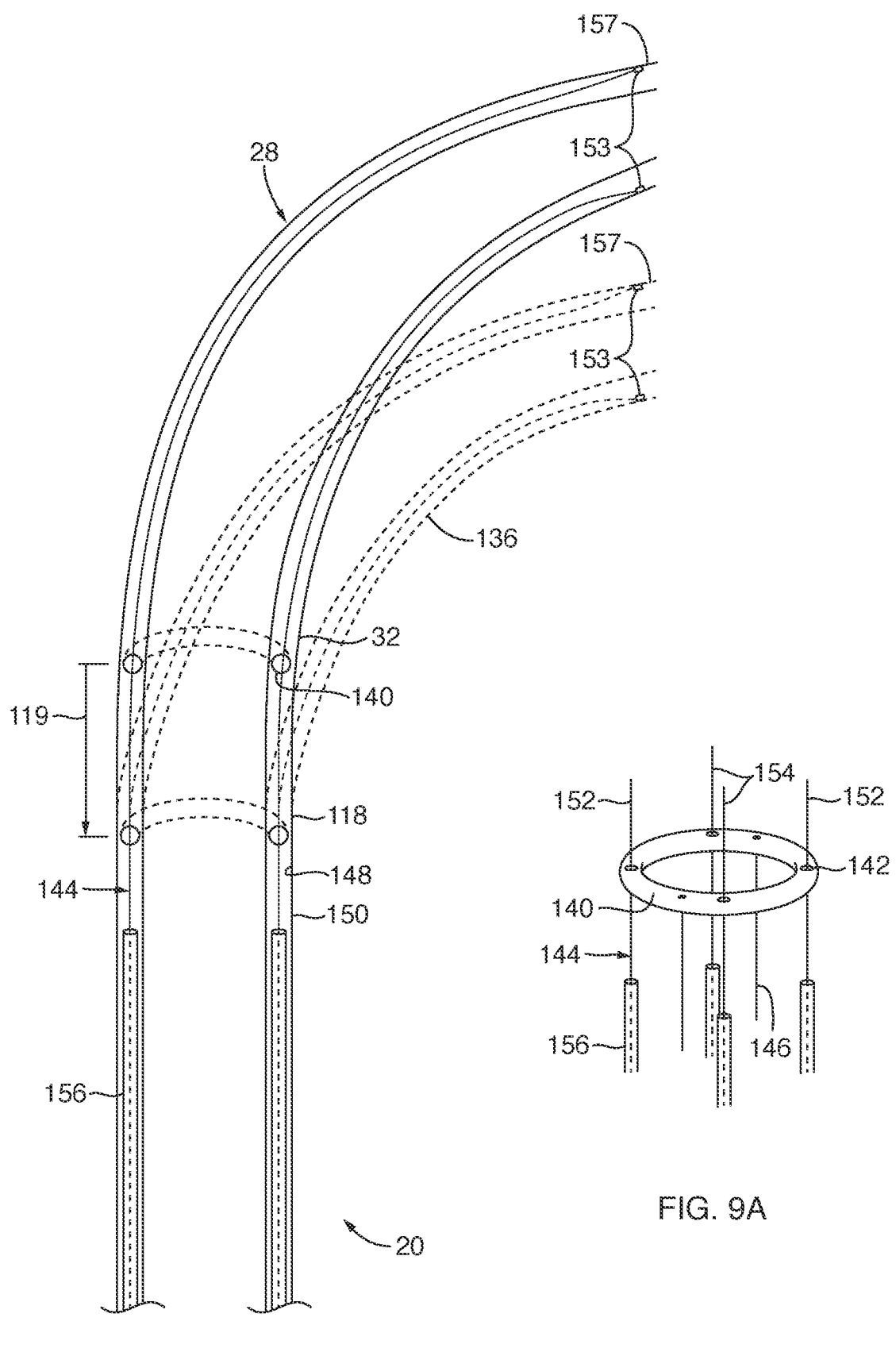
FIG. 9 is a simplified cross-sectional view of the sheath, depicting the first pivot location being adjustable with a ring structure within an annular lumen defined in the sheath, according to another embodiment of the present invention.
FIG. 9A is simplified perspective view of some of the components of the sheath of FIG. 9, depicting some of the components proximate the first pivot location without the sheath, according to another embodiment of the present invention.

Now with reference to FIGS. 8, 9 and 9A, one embodiment of the sheath 20 with the first pivot location 32 being moveable is provided, FIG. 9A depicting some components without the sheath 20. In this embodiment, adjacent the first pivot location 32, the sheath 20 may include a first ring structure 140 with holes 142 defined therein, first actuation wires 144 and first displacement wires 146. The first ring structure 140 may be positioned within an annular lumen 148 defined in a wall 150 of the sheath 20. The first actuation wires 144 may extend through the holes 142 so as to be operatively coupled to the sheath handle 54 at one end and coupled adjacent to a distal most end 157 of the first deflectable portion 28. Such first actuation wires 144 may include x-component wires 152 and y-component wires 154, which also may be referenced as x-plane deflection control wires and y-plane deflection control wires. The x-component wires 152 defining an x-plane and the y-component wires 154 defining a y-plane. Such x-component wires 152 and y-component wires 154 may be operatively coupled to the sheath handle 54 and may be manipulated at the sheath handle 54 with, for example, the first and second knobs 126, 128, to actuate the first deflectable portion 28 to various positions and orientations, similar to that previously described and depicted relative to FIGS. 4-7. For example, with one end of the x-component wires 152 coupled to the distal most end 157 of the first deflectable portion (and oppositely positioned within the annular lumen of the sheath) at the first x-attachment points 153, deflection of the first deflectable portion 28 may be implemented by pulling one x-component wire 152 and pushing the other x-component wire 152 at the sheath handle 54 in order to achieve deflection of the first deflectable portion 28 along the x-plane defined by the x-component wires 152. Similarly, deflection of the first deflectable portion 28 may be implemented by pulling one y-component wire 154 and pushing the other y-component wire 154 at the sheath handle 54 in order to achieve deflection of the first deflectable portion 28 along the y-plane defined by the y-component wires 154. Further, deflection of the first deflectable portion 28 may be implemented by combining the pulling of both one of the x-component wire 152 and y-component wire 154 and pushing the other ones of the x-component wire 152 and the y-component wire 154. Each of the x-component wires 152 and y-component wires 154 may include a stiffening structure formed therearound, such as a coil structure, so that compression or pushing of the x-component wires 152 and the y-component wires 154 may effectively be employed to deflect the first deflectable portion 28.

Further, each of the x-component 152 and y-component wires 154 may extend longitudinally through a lumen of a guide tube 156 for a total of, e.g., four guide tubes, each of the guide tubes 156 also extending longitudinally along the length 22 of the sheath 20 and extending through the annular lumen 148 of the sheath 20. Such guide tubes 156 may provide guidance and support for the first actuation wires 144. Further, in another embodiment, the first actuation wires 144 may include a coil arrangement wrapped or wound around the wires along at least a portion of their respective lengths to provide compression characteristics. With this arrangement, the guide tubes 156 and first actuation wires 144 may be coupled to the sheath handle 54 so as to facilitate actuating the first deflectable portion 28, as previously set forth.

The first displacement wires 146 may extend longitudinally from the first ring structure 140 to, or adjacent to, the sheath handle 54 so as to be operatively coupled to the finger 130 of the sheath handle 54, for example. Such first displacement wires 146 may be sized and configured to move the first ring structure 140 in the proximal direction or distal direction such that the first ring structure 140 may slide along the length 22 of the sheath 20, as depicted by arrow 119 or arrow 121, respectively. The movement of the first ring structure 140 moves or adjusts the first pivot location 32. The first pivot location 32 may correspond with a distal side of the first ring structure 140. Further, movement of the first ring structure 140 or first pivot location 32 enables the physician to adjust the radius of the first deflectable portion 28, as set forth above. Upon the first pivot location 32 being moved proximally to the proximal first pivot location 118, the first deflectable portion 28 may be actuated with a proximal first radius 136. Similarly, upon the first pivot location 32 and first ring structure 140 being moved distally to the distal first pivot location 120, the first deflectable portion 28 may be actuated with a distal first radius 138. In one embodiment, the proximal first radius 136 being larger than the distal first radius 138. In another embodiment, the first displacement wires 146 may include a coil structure associated therewith such that the coil structure facilitates compressive characteristics of the first displacement wires 146. Further, similar to the various components described relative to the first pivot location 32, the second pivot location 34 may include the same or similar components so that the second pivot location 34 may be adjusted proximally and distally to facilitate adjusting a radius of the second deflectable portion 30 as well as be actuated to various positions and orientations similar to that described and depicted relative to FIGS. 4-7, and 9.

Figures 10, 10A:
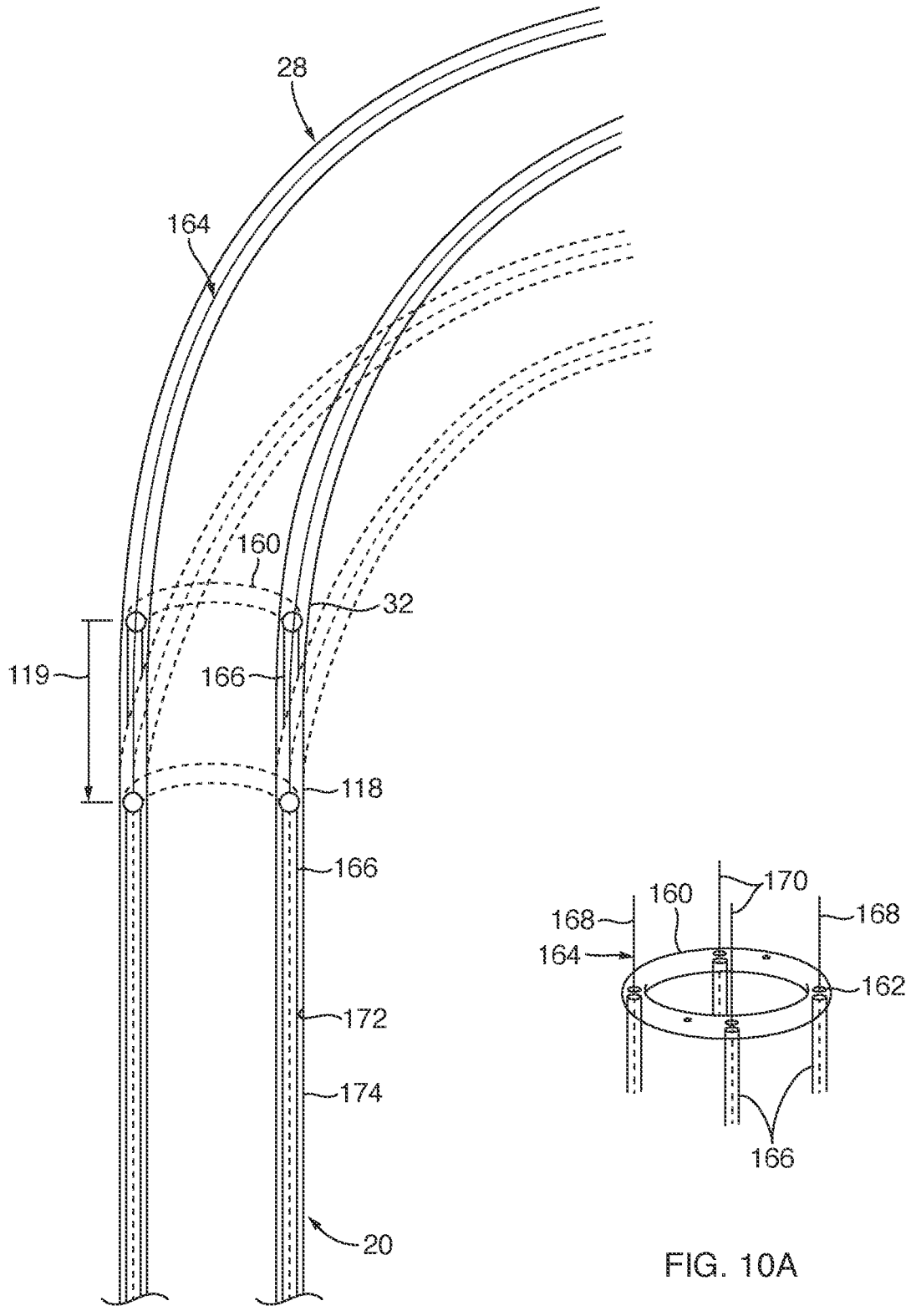
FIG. 10 is a simplified cross-sectional view of another embodiment of the sheath, depicting the first pivot location having a ring structure that is adjustable with tube structures within the annular lumen of the sheath, according to the present invention.
FIG. 10A is a simplified perspective view of some of the components of the sheath of FIG. 10, depicting some of the components proximate the first pivot location without the sheath, according to another embodiment of the present invention.

Now with reference to FIGS. 8, 10 and 10A, another embodiment of the sheath 20 with the first pivot location 32 being moveable is provided, FIG. 10A depicting some components without the sheath 20. The sheath 20, adjacent the first pivot location 32, may include a first ring structure 160 with holes 162 defined therein, first actuation wires 164, and first displacement tubes 166. In this embodiment, instead of first displacement wires and guide tubes as set forth in the previous embodiment, the first displacement tubes 166 may be directly attached to the first ring structure 160 and act as a guide with x-component wires 168 and y-component wires 170 of the first actuation wires 164 extending through the first displacement tubes 166. As set forth in previous embodiments, the first actuation wires 164 may be sized and configured to actuate the first deflectable portion 328. The first displacement tubes 166 may extend longitudinally within an annular lumen 172 defined in a wall 174 of the sheath 20. Further, within the annular lumen 172 of the sheath 20, the first displacement tubes 166 may move proximally and distally, as shown by respective arrows 119 and 121, to directly slide the first ring structure 160 within the sheath 20. The movement of the first ring structure 160 also moves the first pivot location 32 since, as in the previous embodiment, a distal side of the first ring structure 160 corresponds with the first pivot location 32. With this arrangement, the first pivot location 32 may be moved and adjusted between the proximal and distal first pivot locations 118, 120 of the first deflectable portion 28. As set forth in previous embodiments, adjusting the pivot location also may adjust the sizing of a radius of the first deflectable portion 28. In this manner, adjusting the first pivot location 32 proximally or distally with the finger 130 of the sheath handle 54 to facilitate adjusting a radius of the first deflectable portion 28 as well as being actuatable or deflectable with the first actuation wires 164 to various positions and orientations, as previously described relative to FIGS. 4-7. Also, similar to the various components described relative to the first ring structure 160, first displacement tubes 166, etc., described relative to the first pivot location 32, the second pivot location 34 may include the same or similar components so that the second pivot location 34 may be adjusted proximally and distally to facilitate adjusting a radius of the second deflectable portion 30 as well as be actuated to various positions and orientations similar to that described and depicted in FIGS. 4-7.

Figures 11, 11A:
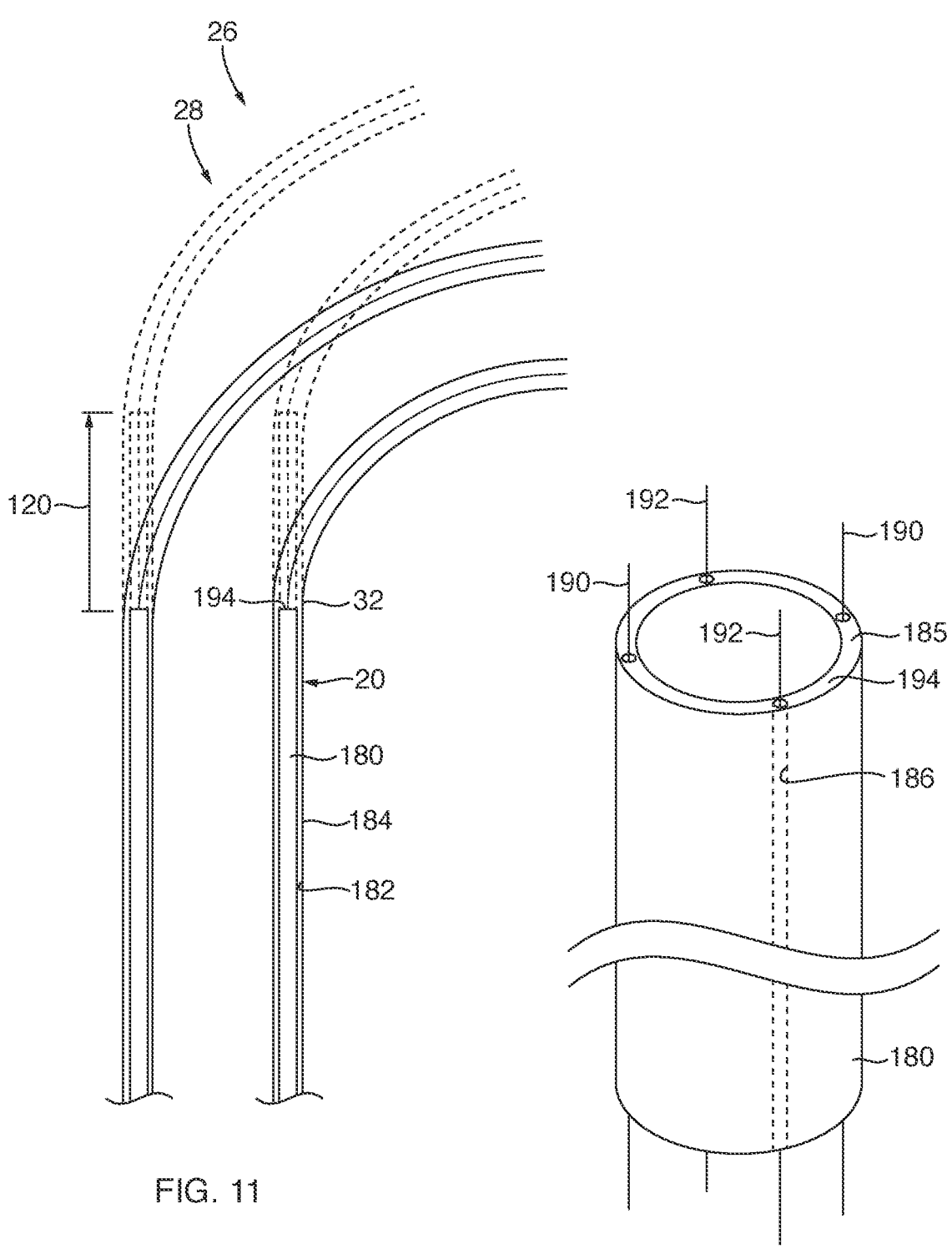
FIG. 11 is a simplified cross-sectional view of another embodiment of the sheath, depicting the first pivot location being adjustable with a tube structure, according to the present invention.
FIG. 11A is a simplified perspective view of some of the components of the sheath of FIG. 11, depicting some of the components proximate the first pivot location without the sheath, according to another embodiment of the present invention.

With reference to FIGS. 8, 11 and 11A, another embodiment of the sheath 20 with the first pivot location 32 being moveable is provided, FIG. 11A depicting some of the components without the sheath 20. In this embodiment, the sheath 20 may include a tubular member 180 sized and configured to be slidingly positioned within an annular lumen 182 defined in a wall 184 of the sheath 20. The tubular member 180 may extend to define a tube wall 185 with multiple channels 186 defined in the tube wall 185.

Each of the channels 186 may extend longitudinally and linearly through the tubular member 180 and along a longitudinal length of the tubular member 180. Further, in one embodiment, the channels 186 may be spaced relative to each other such that two channels 186 may extend through opposite sides of the tube wall 185 and another two channels 186 may also extend through opposite sides of the tube wall so that each of the channels 186 may be spaced about 90 degrees relative to adjacent ones of the channels 186. Such channels 186 may be sized and configured to hold first actuation wires 188, the first actuation wires 188 including x-component wires 190 and y-component wires 192, similar to previous embodiments. The first pivot location 32 may be defined adjacent a distal end 194 of the tubular member 180. Further, the tubular member 180 may be slidingly moveable within the annular lumen 182 of the sheath 20 so as to be moveable between the proximal and distal first pivot locations 118, 120. For example, similar to previous embodiments, the distal end 194 of the tubular member 180 may be moveable and, thus, the first pivot location 32 (which is adjacent the distal end 194) may be moveable distally by moving the finger 130 of the sheath handle 54 distally to thus move the first pivot location 32 to the distal first pivot location 120. In this manner, a physician may adjust the pivot location anywhere between the proximal and distal first pivot locations 118, 120 of the first deflectable portion 28 and, thus, adjust a radius of the first deflectable portion 28. Further, as in previous embodiments, the second pivot location 34 may be adjusted with similar components and functionality as the first pivot location 32 so as to adjust the pivot location and radius of the second deflectable portion 30. In this manner, the distal end portion 26 of the sheath 20 may include the first and second deflectable portions 28, 30 that may each be adjusted to modify the radius by which the first and second deflectable portions 28, 30 may be actuated.

Figure 12:
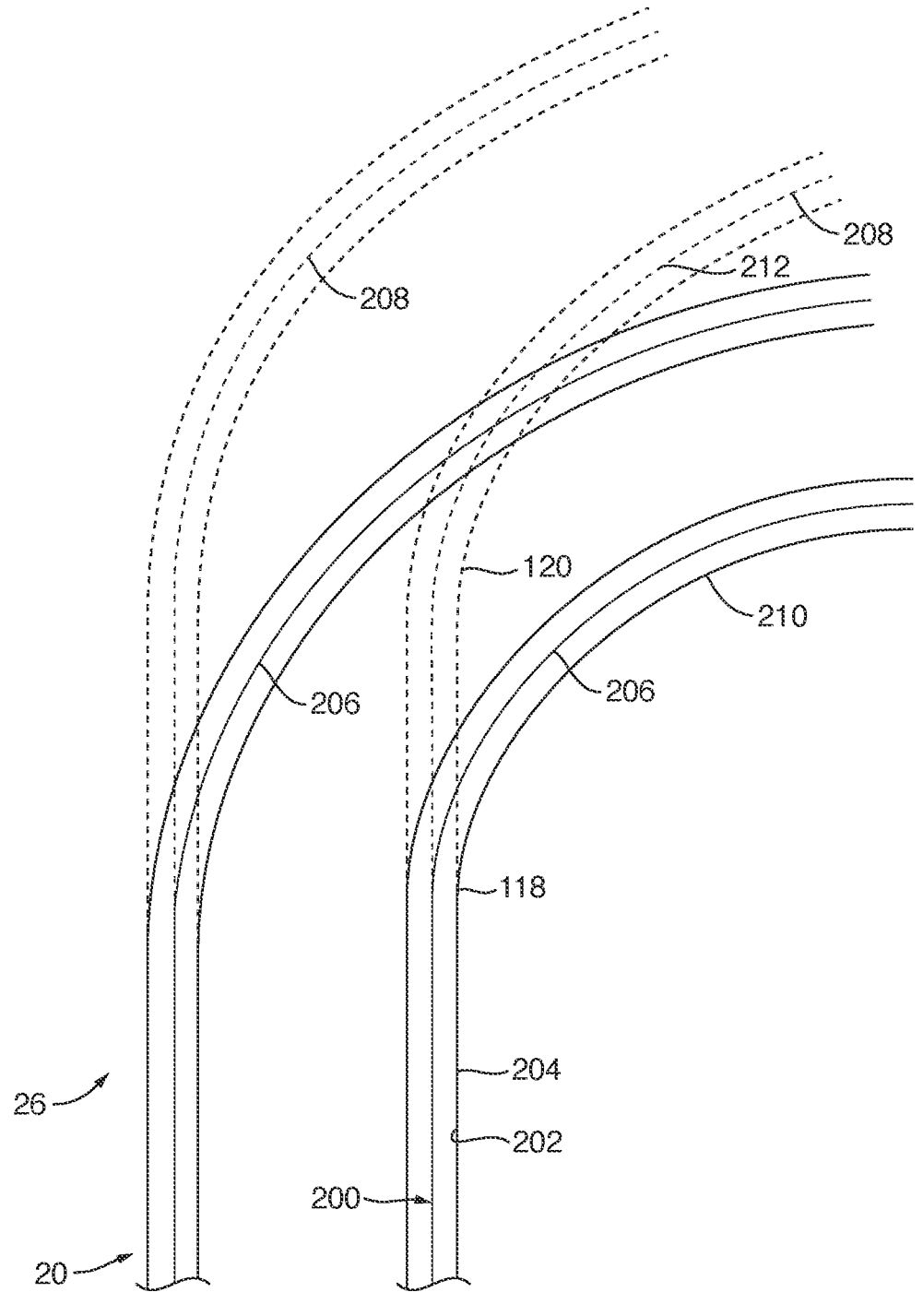
FIG. 12 is a simplified cross-sectional view of another embodiment of the sheath, depicting the first pivot location of the sheath being adjustable with one or more wires, according to the present invention.

With reference to FIGS. 8 and 12, another embodiment of the distal end portion 26 of the sheath 20 is provided. In this embodiment, the sheath 20 may include multiple Nitinol wires 200 sized and configured to change their configuration between relaxed and constrained positions. For example, movement between relaxed and constrained positions of the Nitinol wires may be employed by controlling various pre-defined energy settings to control deflection and/or a radius of curvature of the first and second deflectable portions 28, 30 along the distal end portion 26 of the sheath 20. The multiple Nitinol wires 200 may extend through the annular lumen 182 defined in the wall 204 of the sheath 20. In one embodiment, the first deflectable portion 28 may be adjustable in its pivot location between the proximal first pivot location 118 and the distal first pivot location 120 that may correspond with different deflectable lengths and different radiuses, similar to that previously set forth. In another embodiment, as depicted in FIG. 12, the Nitinol wires 200 of the first deflectable portion 28 may include first wires 206 and second wires 208, the first wires 206 configured to move to the constrained position with a first radius 210 that may correspond with the proximal first pivot location 118. Similarly, the second wires 208 may be configured to move to the constrained position with a second radius 212 that may correspond with the distal first pivot location 120. In another embodiment, similar to that set forth for the first deflectable portion 28, the sheath 20 may include third wires and fourth wires (not shown), the third wires configured to move to the constrained position with a pre-defined energy setting to move the second deflectable portion 30 to exhibit one radius that may correspond with a proximal second pivot location and the fourth wires configured to move to the constrained position with a pre-defined energy setting to move the second deflectable portion to exhibit another radius that may correspond with a distal second pivot location (not shown). In another embodiment, the actuation wires, described and depicted in previous embodiments, may be employed with the multiple Nitinol wires 200 for further control of the first and second deflectable portions 28, 30. In another embodiment, the annular lumen 202 may include multiple Nitinol wires 200 such that each of the Nitinol wires may be sized and configured to be moved to a single pre-defined constrained shape upon being energized or activated. In another embodiment, the first and second deflectable portions 28, 30 of the sheath 20 may be moved to various pre-defined constrained shapes, each of which may be implemented by at least two Nitinol wires 200. In another embodiment, at least some of the Nitinol wires 200 may be moved to multiple pre-defined constrained shapes, dependent upon an energy level applied to one or more Nitinol wires. With this arrangement, the first and second deflectable portions 28, 30 may be actuated to various positions and orientations as well as to various sized radiuses, deflectable lengths and to various pivot locations so that the distal end 110 of the sheath 20 may be manipulated by a physician to an appropriate orientation for implanting a medical device in an opening, such as the left atrial appendage.

Figure 13:
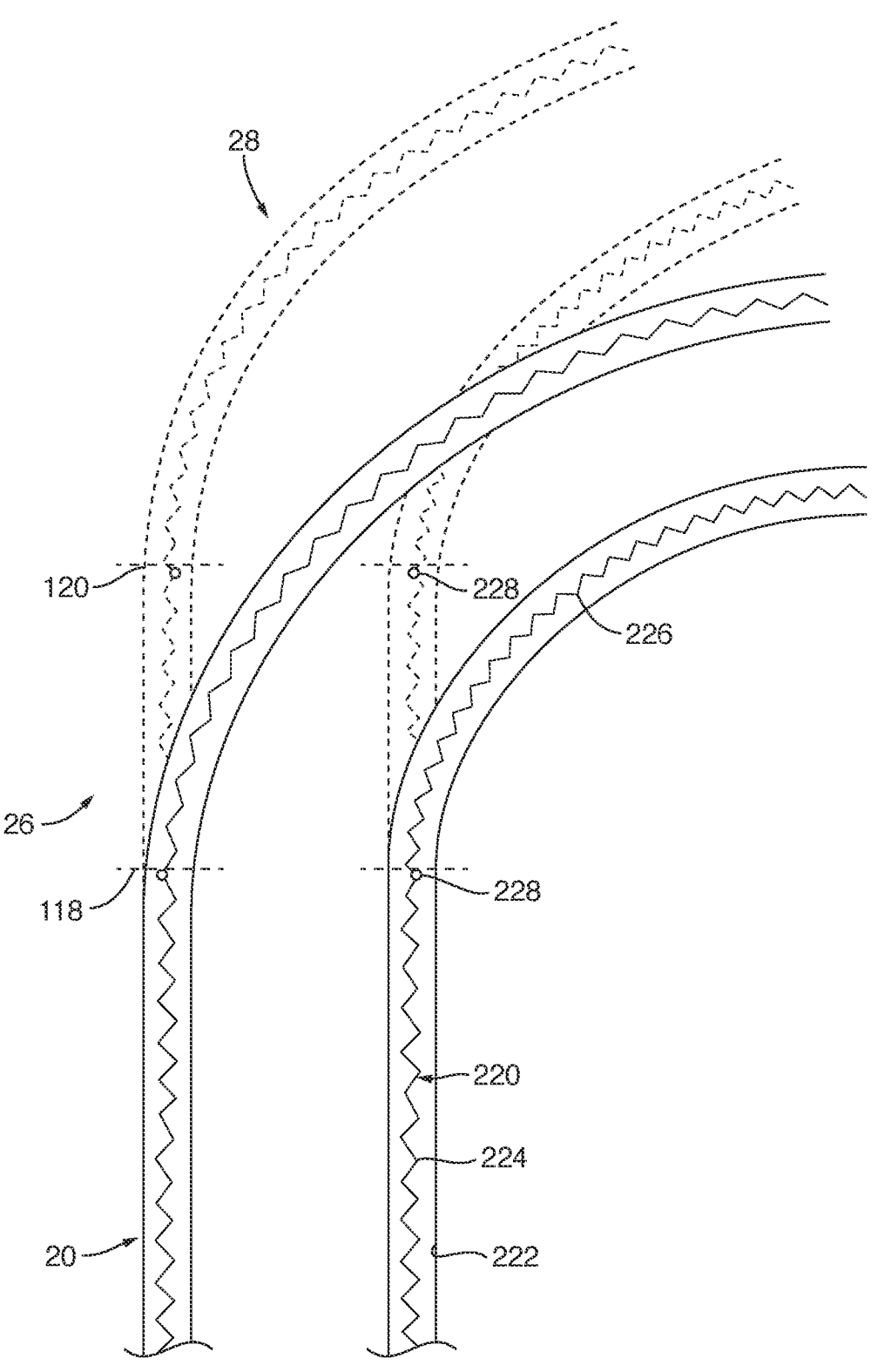
FIG. 13 is a simplified cross-sectional view of another embodiment of the sheath, depicting the first pivot location of the sheath being adjustable with one or more spring members, according to the present invention.

Now with reference to FIGS. 8 and 13, another embodiment of the distal end portion 26 of the sheath 20 is provided. In this embodiment, the first and second deflectable portions 28, 30 may each be adjusted with different radiuses by employing multiple wires 220 with varying stiffness along their lengths that may extend within an annular lumen 222 of the sheath 20. For example, as depicted in FIG. 13, the first deflectable portion 28 at the distal end portion 26 of the sheath 20 may include multiple wires 220, each of which may include a stiff portion 224 and a flexible portion 226. A transition 228 between the stiff portion 224 and the flexible portion 226 may correspond with the first pivot location 32, the flexible portion 226 of the wires 220 facilitating actuation of the first deflectable portion 28. As in previous embodiments, such first pivot location 32 may be moved between the proximal first pivot location 118 and the distal first pivot location 120, which may be employed by moving the wires 220 so that the transition 228 moves proximally or distally, as desired. Further, as in previous embodiments, the proximal and distal first pivot locations 118, 120 may correspond with different radiuses by which the first deflectable portion may be actuated. Although FIG. 13 only depicts different radiuses of the first deflectable portion 28, the sheath 20 may also include wires 220 with stiff and flexible portions that may correspond and be implemented along the second deflectable portion 30. Further, as set forth in previous embodiments, the first and second deflectable portions 28, 30 may be actuated with actuation wires with x-component and y-component wires, similar to that depicted and described relative to FIGS. 4-7 and 9.

With reference to FIG. 8, actuation of the first and second deflectable portions 28, 30 may be employed at the sheath handle 54 with, for example, the first and second knobs 126, 128. The first and second knobs 126, 128 of the sheath handle 54 may be integrated with internal structure 230 (see FIGS. 14A, 14B) to move the actuation wires 144, 164, 188 along the longitudinal length 22 of the sheath 20 (longitudinal movement) as set forth in the embodiments described relative to FIGS. 9, 9A, 10, 10A, 11 and 11A. Further, as set forth herein, such actuation wires 144, 164, 188 may include first and second actuation wires sized and configured to be associated with the respective first and second deflectable portions 28, 30, respectively. Also, the first and second actuation wires may each include x-component wires and y-component wires that may be associated with both the first and second deflectable portions 28, 30. In this manner, the first and second knobs 126, 128 of the sheath handle 54 may be rotated to actuate the internal structure 230 (FIGS. 14A, 14B) of the sheath handle 54, for example. Such internal structure 230 of the sheath handle 54 may include mechanical mechanisms, electrical mechanisms, pneumatic mechanisms, hydraulic mechanisms and/or magnetic mechanisms to employ longitudinal movement of the actuation wires 144, 164, 188, as known to one of ordinary skill in the art.

Figure 14A:
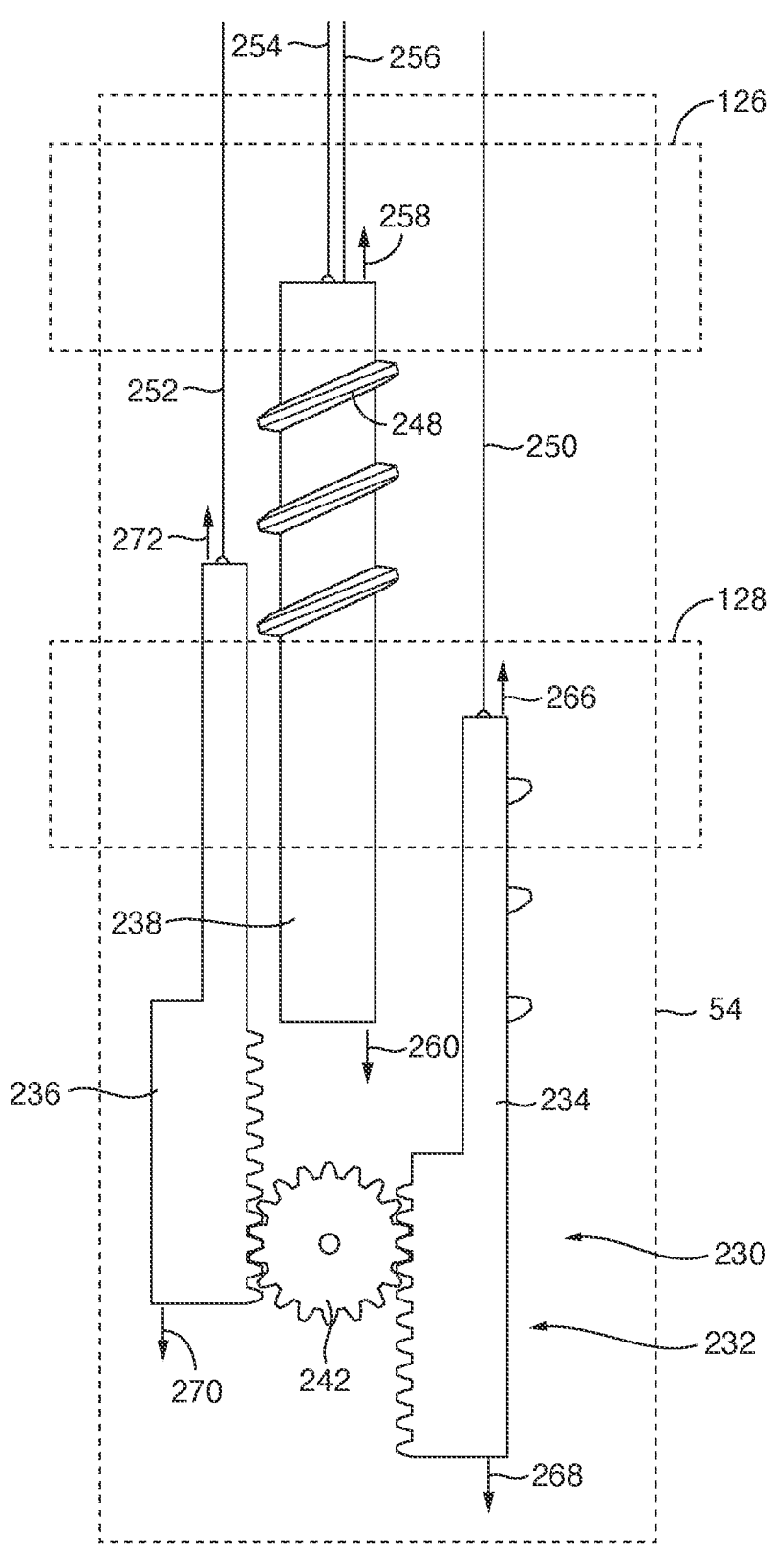
FIG. 14A is a front view of internal structure of a sheath handle, depicting the sheath handle having a rack and pinion system, according to another embodiment of the present invention.
Figure 14B:
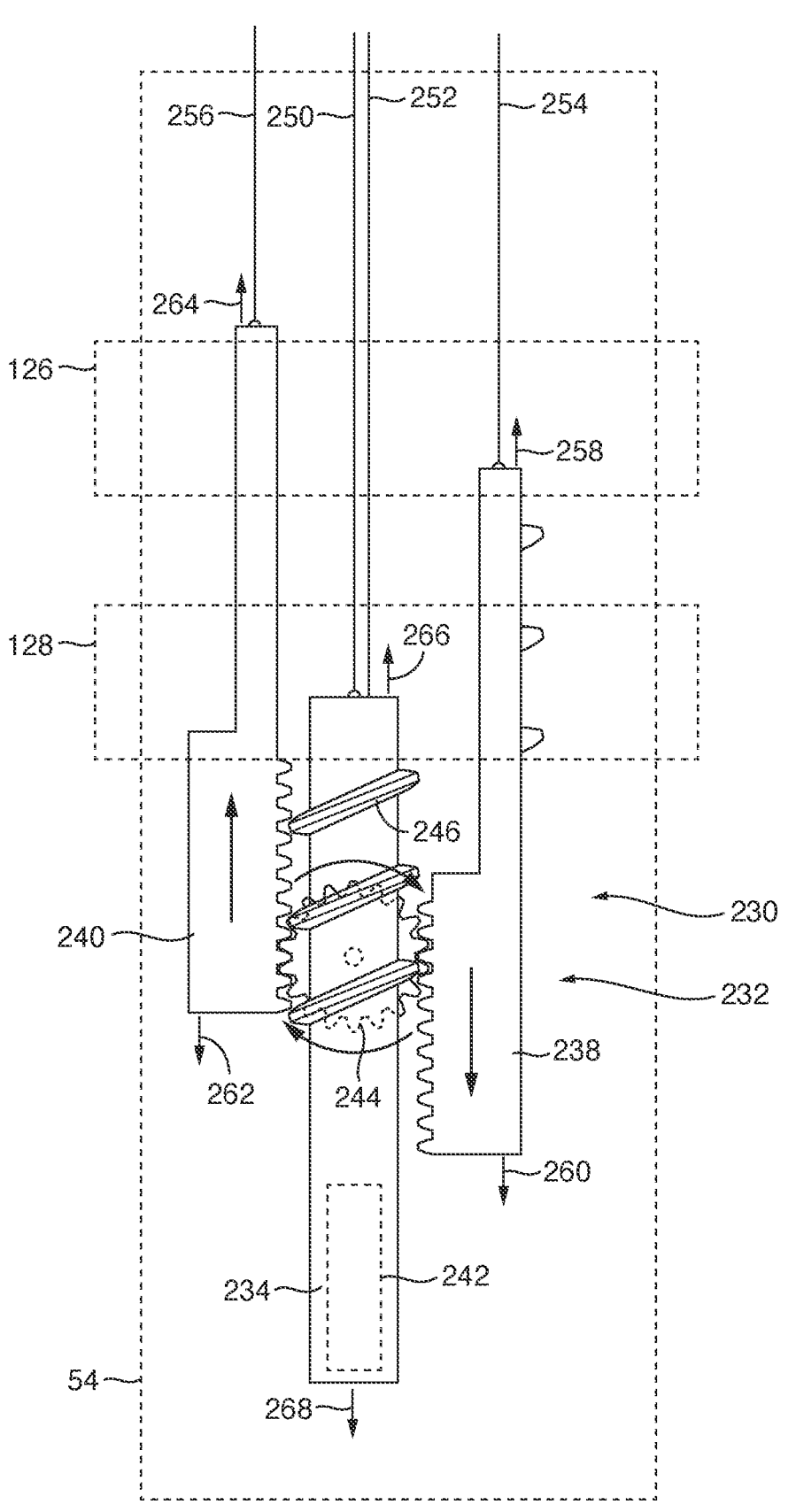
FIG. 14B is a side view of the internal structure of the sheath handle of FIG. 14A, depicting components of the rack and pinion system of the sheath handle, according to another embodiment of the present invention.

For example, with reference to FIGS. 14A and 14B, one embodiment of the internal structure 230 of the sheath handle 54 with the first and second knobs 126, 128 is provided. In this embodiment, the internal structure 230 may be in the form of a mechanical mechanism, such as a rack and pinion system 232, integrated with the sheath handle 54. The rack and pinion system 232 may include first and second x-racks 234, 236, first and second y-racks 238, 240, an x-pinion 242, and a y-pinion 244. The first x-rack 234 may include x-rack threads 246 along a surface thereof and the first y-rack 238 may also include y-rack threads 248. Further, the x-pinion 242 may be positioned between the first and second x-rack 234, 236 and, in a similar manner, the y-pinion 244 may be positioned between the first and second y-rack 238, 240. The x-pinion 242 and y-pinion 244 may include gears to engage rack gearing for effective opposite linear movement of the first and second x-racks 234, 236 and the first and second y-racks 238, 240, as known to one of ordinary skill in the art. Furthermore, the first and second x-racks 234, 236 may be coupled to respective first and second x-component wires 250, 252 at distal ends thereof. Likewise, the first and second y-racks 238, 240 may be coupled to respective first and second y-component wires 254, 256 at the distal ends thereof. The first and second x-component wires 250, 252 and the first and second y-component wires 254, 256 depicted in FIGS. 14A and 14B may be employed as the x-component wires and y-component wires discussed and described in previous embodiments herein, e.g., FIGS. 9, 9A, 10, 10A, 11 and 11A.

As the first knob 126 (which also may be referenced as a y-knob) may be rotated, the first knob 126 engages the first y-rack threads 248 such that clockwise rotation of the first knob 126 may move the first y-rack upward or distally, as shown by arrow 258, and counter-clockwise rotation of the first knob may move the first y-rack downward or proximally, as shown by arrow 260. As the first y-rack 238 moves distally, the second y-rack 240 may move in the opposite direction, shown by arrow 262, via the y-pinion 244 positioned between the first and second y-racks 238, 240. If the first y-rack 238 moves proximally, then the second y-rack 240 may move in the opposite direction, as shown by arrow 264, due to the y-pinion 244 positioned between the first and second y-racks 238, 240.

Similarly, as the second knob 128 (also referenced as an x-knob) is rotated, the second knob engages the first x-rack threads 246 such that clockwise rotation of the second knob 128 may move the first x-rack 234 upward or distally, as shown by arrow 266, and counter-clockwise rotation of the second knob 128 may move the first x-rack 234 downward or proximally, as shown by arrow 268. As the first x-rack 234 moves distally or proximally, the second x-rack 236 may move in the opposite direction, see respective proximal arrow 270 and distal arrow 272, via the x-pinion 242 positioned between the first and second x-racks 234, 236. As the first and second x-racks 234, 236 move proximally or distally and as the first and second y-racks 238, 240 move proximally or distally, each of the first and second x-component wires 250, 252 and the first and second y-component wires 254, 256 also move proximally or distally. In this manner, a rack and pinion system 232 may be employed as the inner structure 230 to the sheath handle 20 such that a physician may rotate first and second knobs 126, 128 to respectively deflect the first deflectable portion 28 and, in a similar manner, the second deflectable portion 30 by moving, for example, the switch 132, as previously set forth herein (see FIG. 8).

Figures 15A, 15B:
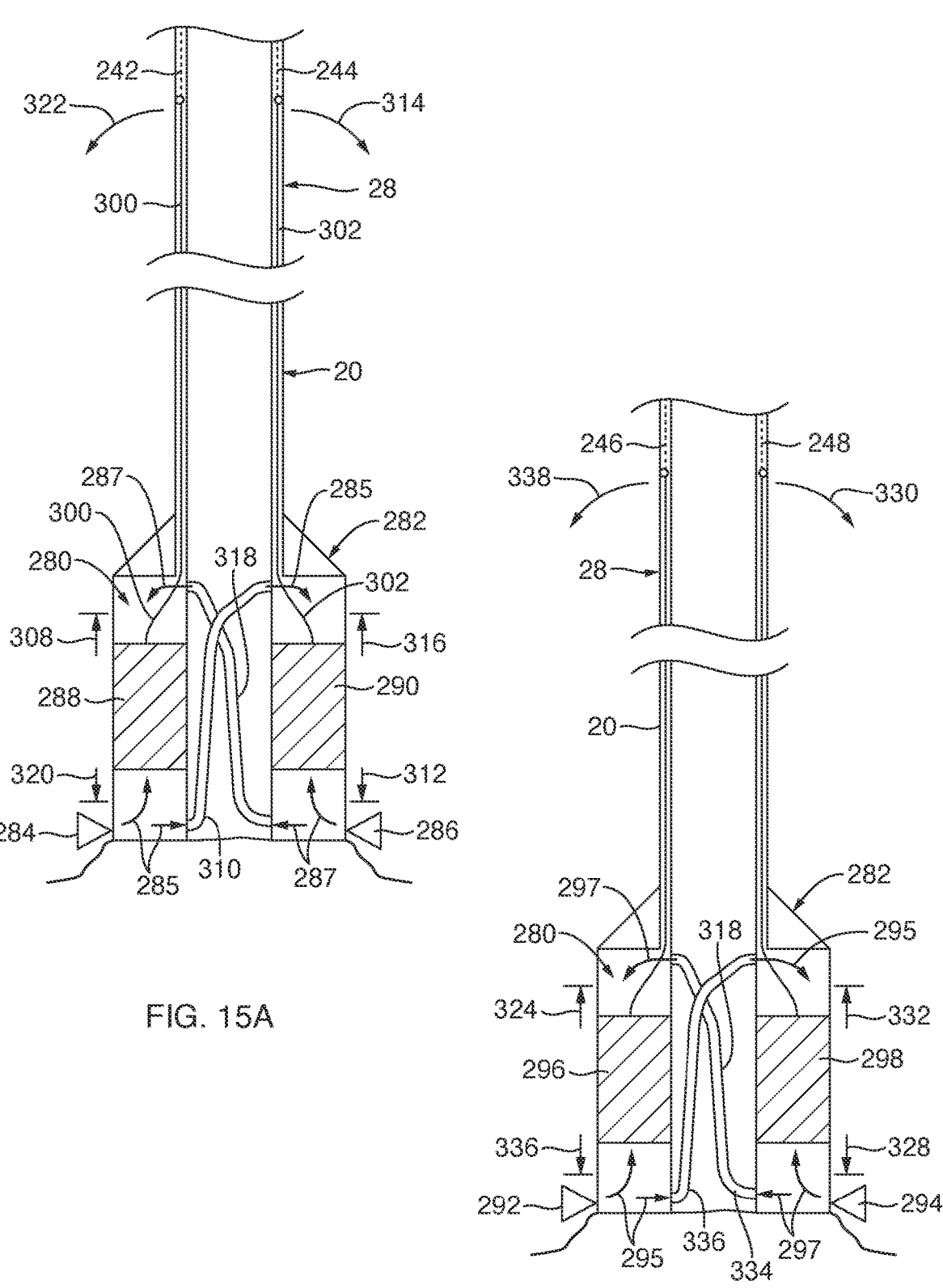
FIG. 15A is a cross-sectional front view of another embodiment of internal structure of a sheath handle, depicting the internal structure having a pneumatic or hydraulic system, according to another embodiment of the present invention.
FIG. 15B is a cross-sectional side view of the internal structure of the sheath handle of FIG. 15A, according to another embodiment of the present invention.

Now with reference to FIGS. 15A and 15B, another example of an embodiment of the internal structure 280 of a sheath handle 282 coupled to the sheath 20 is provided. In this embodiment, the sheath handle 282 includes a pneumatic or hydraulic mechanisms for deflecting first and second deflectable portions 28, 30 (FIG. 8). The sheath handle 282 includes first and second x-injection ports 284, 286 that may be associated with first and second x-pistons 288, 290 as well as first and second y-injection ports 292, 294 that may be associated with first and second y-pistons 296, 298. Furthermore, each piston may be associated with one or more actuation or deflection wires. For example, the first x-piston 288 may be coupled to a first x-component wire 300 and the second x-piston 290 may be coupled to a second x-component wire 302. Similarly, the first and second y-pistons 296, 298 may be coupled to first and second y-component wires 304, 306. The injection ports and pistons of the sheath handle 282 may function with additional structure, such as various valves, seals, etc., as known to one of ordinary skill in the art.

Referring to FIG. 15A, upon the first x-injection port 284 being activated, fluid flow (such as air or hydraulic fluid), as shown by arrow 285, may move against the proximal side of the first x-piston 288 to displace the first x-piston 288 distally as shown by displacement arrow 308. Further, as the first x-injection port 284 is activated, fluid flow may move through a first line 310 to a distal side of the second x-piston 290 to displace the second x-piston proximally, as shown by displacement arrow 312. The distal displacement of the first x-piston moves the first x-component wire 300 in a distal direction and the proximal displacement of the second x-piston 290 moves the second x-component wire 302 in a proximal direction, which may deflect the first deflectable portion 28 in one direction, as shown by deflection arrow 314. In a similar manner, upon the second x-injection port 286 being activated, fluid flow, as shown by arrow 287, moves against the proximal side of the second x-piston 290 to displace the second x-piston distally, as shown by displacement arrow 316, and, with the second x-injection port 286 activated, fluid may flow, as shown by arrow 287, through a second line 318 to a distal side of the first x-piston 288 to displace the first x-piston 288 proximally, as shown by displacement arrow 320. With the distal displacement of the second x-piston 290 and the proximal displacement of the first x-piston 288, such displacement also moves the respective first x-component wire 300 proximally and the second x-component wire 302 distally, which in turn may deflect the first deflectable portion 28 in another direction, as shown by deflection arrow 322. In this manner, the first deflectable portion 28 may be moveable within an x-plane, defined by the first and second x-component wires 300, 302.

Now referring to FIG. 15B, in a similar manner to that previously set forth relative to movement of the first deflectable portion 28 moveable in the x-plane, the first deflectable portion 28 may also be moveable in a y-plane defined by the first and second y-component wires 304, 306. For example, upon the first y-injection port 292 being activated, fluid flow, as shown by arrow 295, moves against the proximal side of the first y-piston 296 to displace the first y-piston 292 distally as shown by displacement arrow 324. Further, as the first y-injection port 292 is activated, fluid flow, as shown by arrow 295, moves through a first y-line 326 to a distal side of the second y-piston 298 to displace the second y-piston 298 proximally, as shown by displacement arrow 328. The distal displacement of the first y-piston 296 moves the first y-component wire 304 in a distal direction and the proximal displacement of the second y-piston 298 moves the second y-component wire 306 in a proximal direction, which may deflect the first deflectable portion 28 in one direction, as shown by deflection arrow 330. In a similar manner, upon the second y-injection port 294 being activated, fluid flow, as shown by arrow 297, moves against the proximal side of the second y-piston 298 to displace the second y-piston 298 distally, as shown by displacement arrow 332, and, with the second y-injection port 294 activated, fluid may flow, as shown by arrow 297, through a second y-line 334 to a distal side of the first y-piston 296 to displace the first y-piston 296 proximally, as shown by displacement arrow 336. With the distal displacement of the second y-piston 298 and the proximal displacement of the first y-piston 296, such displacement also moves the respective first y-component wire 304 proximally and the second y-component wire 306 distally, which in turn may deflect the first deflectable portion 28 in another direction, as shown by arrow 338. As such, the first deflectable portion 28 may be moveable along the y-plane defined by the first and second y-component wires 304, 306. As in previous embodiments, both the first and/or second x-injection ports 284, 286 and the first and/or second y-injection ports 292, 294 may be activated to deflect the first deflectable portion 28 in an orientation positioned between the x-plane and the y-plane, similar to the out-of-plane deflection 240 of the first deflectable portion 28, shown in FIG. 7. Furthermore, in another embodiment, deflection of the second deflectable portion 30 may be implemented with additional pistons integrated within the sheath handle 282 to be employed in a similar manner to that set forth above to, thereby, move first and second x-wires 242, 244 and first and second y-wires 246, 248 for deflecting the second deflectable portion 30 (FIG. 8). In another embodiment, the sheath handle 282 may include a switch (similar to switch 132 of FIG. 8) that may facilitate changing each of the depicted first and second x-pistons 288, 290 and the first and second y-pistons 296, 298 to be associated with the second deflectable portion 30. In this manner, a physician may employ the sheath handle 282 to manipulate the orientation of the distal end portion 26 of the sheath 20 with functionality of deflecting the first and second deflectable portions 28, 30, similar to that depicted and described in FIGS. 4-8.

As set forth, embodiments of a mechanical mechanism (FIGS. 14A, 14B) and a pneumatic/hydraulic mechanism (FIGS. 15A, 15B) in a sheath handle for implementing longitudinal movement of actuation wires to controllably deflect portions of a sheath have been described. However, as previously indicated, the sheath handle may include other mechanisms, such as electrical components and/or magnetic mechanisms as well as other types of mechanical mechanisms, to facilitate longitudinal movement of the actuation wires to controllably deflect the sheath, as known to one of ordinary skill in the art.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention includes incorporating any portion of one embodiment with another embodiment, all modifications, equivalents, and alternatives falling within the spirit and scope of the invention as defined by the following appended claims.

What is claimed is:

1. A medical device system for occluding a left atrial appendage of a heart, comprising;

a delivery catheter with a medical device coupled adjacent a delivery catheter distal end of the delivery catheter; and a sheath having a sheath handle with a pivot location member, the pivot location member moveable linearly distal and linearly proximal relative to the sheath handle, the sheath extending with a wall between a distal end and a proximal end with a central lumen and central axis defined in the sheath along a longitudinal length of the sheath such that the medical device and delivery catheter are advanceable through the central lumen of the sheath, the sheath defining a concentric lumen therein so as to extend along the wall, the sheath being deflectable with a first deflectable portion relative to a first pivot location along a distal portion of the sheath and the sheath being deflectable with a second deflectable portion relative to a second pivot location along the distal portion of the sheath;

wherein, upon advancement of the sheath to the left atrial appendage of the heart, at least one of the first pivot location and the second pivot location of the first and second deflectable portions, respectively, is adjustable with longitudinal movement along the longitudinal length of the distal portion of the sheath;

wherein the at least one of the first and second pivot locations is moveable distally with linear movement of the pivot location member to a distal position; and wherein the at least one of the first and second pivot locations is moveable proximally with linear movement of the pivot location member to a proximal position.

2. The medical device system of claim 1, wherein, upon the at least one of the first and second pivot locations being adjusted, a radius of at least one of the first and second deflectable portions is adjusted.

3. The medical device system of claim 2, wherein the radius increases upon the at least one of the first and second pivot locations being moved proximally along the length of the sheath and, wherein the radius decreases upon the at least one of the first and second pivot locations being moved distally along the length of the sheath.

4. The medical device system of claim 1, wherein the sheath comprises a slidable tubular member with a distal end, the slidable tubular member positioned within the concentric lumen defined in the sheath, the distal end of the slidable tubular member defining at least one of the first and second pivot locations of the sheath.

5. The medical device system of claim 4, wherein the slidable tubular member is linearly slideable within the concentric lumen to change the at least one of the first and second pivot locations of the sheath.

6. The medical device system of claim 4, wherein the slidable tubular member includes openings defined therein, the openings sized and configured to hold control wires therein so that the control wires extend distal of at least one of the first and second pivot locations for controlling deflection of at least one of the first and second deflectable portions, respectively.

7. The medical device system of claim 1, wherein the first and second deflectable portions are deflectable in multiple directions.

8. The medical device system of claim 1, wherein the sheath is separately and independently deflectable relative to the first pivot location and the second pivot location along the sheath.

9. The medical device system of claim 1, wherein the first and second deflectable portions are deflectable with a control actuator integrated in the sheath handle of the sheath, the control actuator including at least one of a rack and pinion system, a pneumatic system, and a hydraulic system.

10. The medical device system of claim 1, wherein at least one of the first and second deflectable portions are deflectable with multiple wires extending through the concentric lumen along the longitudinal length of the sheath, the multiple wires having a first portion and a second portion with a transition point between the first and second portions, the first portion being distal of and more flexible than the second portion, the transition point of the multiple wires being moveable along the longitudinal length to change a radius of the at least one of the first and second deflectable portions.

11. A medical device system for occluding a left atrial appendage of a heart with an implant, the implant positioned adjacent a delivery catheter, comprising;

a sheath having a sheath handle with a pivot location member, the pivot location member moveable linearly distal and linearly proximal relative to the sheath handle, the sheath extending with a wall between a distal end and a proximal end with a central lumen and central axis defined in the sheath along a longitudinal length of the sheath such that the implant and delivery catheter are advanceable through the central lumen of the sheath, the sheath defining a concentric lumen therein so as to extend along the wall, the sheath being deflectable with a first deflectable portion relative to a first pivot location along a distal portion of the sheath and the sheath being deflectable with a second deflectable portion relative to a second pivot location along the distal portion of the sheath;

wherein, upon advancement of the sheath to the left atrial appendage of the heart, at least one of the first pivot location and the second pivot location of the first and second deflectable portions, respectively, is adjustable with longitudinal movement along the longitudinal length of the distal portion of the sheath;

wherein the at least one of the first and second pivot locations is moveable distally with linear movement of the pivot location member to a distal position; and wherein the at least one of the first and second pivot locations is moveable proximally with linear movement of the pivot location member to a proximal position.

12. The medical device system of claim 11, wherein, upon the at least one of the first and second pivot locations being adjusted, a radius of at least one of the first and second deflectable portions is adjusted.

13. The medical device system of claim 12, wherein the radius increases upon the at least one of the first and second pivot location being moved proximally along the length of the sheath and, wherein the radius decreases upon the at least one of the first and second pivot location being moved distally along the length of the sheath.

14. The medical device system of claim 11, wherein the sheath comprises a slidable tubular member with a distal end, the slidable tubular member positioned within the concentric lumen defined in the sheath, the distal end of the slidable tubular member defining at least one of the first and second pivot locations of the sheath.

15. The medical device system of claim 14, wherein the slidable tubular member is linearly slideable within the concentric lumen to change the at least one of the first and second pivot locations of the sheath.

16. The medical device system of claim 14, wherein the slidable tubular member includes openings defined therein, the openings sized and configured to hold control wires therein so that the control wires extend distal of at least one of the first and second pivot locations for controlling deflection of at least one of the first and second deflectable portions, respectively.

17. The medical device system of claim 11, wherein the first and second deflectable portions are deflectable in multiple directions.

18. The medical device system of claim 11, wherein the sheath is separately and independently deflectable relative to the first pivot location and the second pivot location along the sheath.

19. The medical device system of claim 11, wherein the first and second deflectable portions are deflectable with a control actuator integrated in the sheath handle of the sheath, the control actuator including at least one of a rack and pinion system, a pneumatic system, and a hydraulic system.

20. The medical device system of claim 11, wherein at least one of the first and second deflectable portions are deflectable with multiple wires extending through the concentric lumen along the longitudinal length of the sheath, the multiple wires having a first portion and a second portion with a transition point between the first and second portions, the first portion being distal of and more flexible than the second portion, the transition point of the multiple wires being moveable along the longitudinal length to change a radius of the at least one of the first and second deflectable portions.

* * * * *